(12) United States Patent
Daeyaert et al.

(10) Patent No.: US 6,774,235 B2
(45) Date of Patent: Aug. 10, 2004

(54) TRISUBSTITUTED 1,3,5-TRIAZINE DERIVATIVES

(75) Inventors: Frederik Frans Desiré Daeyaert, Antwerpen (BE); Bart De Corte, Southampton, PA (US); Marc René De Jonge, Tilburg (NL); Jan Heeres, Vosselaar (BE); Chih Yung Ho, Lansdale, PA (US); Paul Adriaan Jan Janssen, Vosselaar (BE); Robert W. Kavash, Glenside, PA (US); Lucien Maria Henricus Koymans, Turnhout (BE); Michael Joseph Kukla, Maple Glen, PA (US); Donald William Ludovici, Quakertown, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 10/067,383

(22) Filed: Feb. 5, 2002

(65) Prior Publication Data

US 2002/0115668 A1 Aug. 22, 2002

Related U.S. Application Data

(62) Division of application No. 09/634,340, filed on Aug. 8, 2000, which is a division of application No. 09/276,362, filed on Mar. 25, 1999, now Pat. No. 6,150,360.
(60) Provisional application No. 60/079,633, filed on Mar. 27, 1998.

(51) Int. Cl.[7] .......................................... C07D 251/66
(52) U.S. Cl. ...................................................... 544/208
(58) Field of Search ........................................ 544/208

(56) References Cited

U.S. PATENT DOCUMENTS

| | | | |
|---|---|---|---|
| 2,671,810 A | 3/1954 | Coffman et al. | 260/593 |
| 2,742,466 A | 4/1956 | Randall et al. | 260/249.5 |
| 3,755,322 A | 8/1973 | Winter et al. | 260/249.6 |
| 4,096,206 A | 6/1978 | Boyer | 260/880 |
| 4,652,645 A | 3/1987 | Stingelin et al. | 544/198 |
| 6,107,301 A | 8/2000 | Aldrich et al. | |
| 6,342,503 B1 | 1/2002 | Aldrich et al. | |

FOREIGN PATENT DOCUMENTS

| | | | |
|---|---|---|---|
| DE | 2705415 | | 8/1977 |
| EP | 145656 | | 6/1985 |
| EP | 541966 | | 5/1993 |
| EP | 795549 | | 9/1997 |
| FR | 2099730 | | 3/1972 |
| WO | WO 94/00513 | | 1/1994 |
| WO | WO 97/10887 | * | 3/1997 |

OTHER PUBLICATIONS

Pandya et al., Chem Abstract 126 115472.
Pandya et al., J. Inst. Chemists, 1976.
Pandya et al., Chem Abstract 86:189868.
Acharya et al., Chem Abstract 85:94319.
Acharya et al., Chem Abstract 85:21302.
Prakash et al., Pharmazie 45:284, 1990.
Ashley et al., J. Chem Society (1960), 4525–32.
Shaila et al., Chem Abstract 112:7458v, Jan. 1, 1990.
Kreutzberger et al., Chem Abstract 108:131766a, Apr. 11, 1988.
Langalia et al., Chem Abstract 98 89321z, Mar. 14, 1983.
Unishi et al., Chem Abstract 95:2568b, Jul. 27, 1981.
Kozlova et al., Chem Abstract 57:11216f, (1962).
Honda CHem Abstract 58:4568d, (1963).
Kutepov et al., Chem Abstract 58:4569a, (1963).
Chase et al., Chem Abstract 60:15770h, (1965).
Kozlava et al., Chem Abstract 60:5498h, (1964).
Strukov et al., Chem Abstract 63:4127a, (1965).
Honda et al., Chem Abstract 63:4298h, (1965).
Parasharya et al., Chem Abstract 108:112399s, (1988).

(List continued on next page.)

Primary Examiner—Mukund J. Shah

(57) ABSTRACT

This invention concerns the use of the compounds of formula

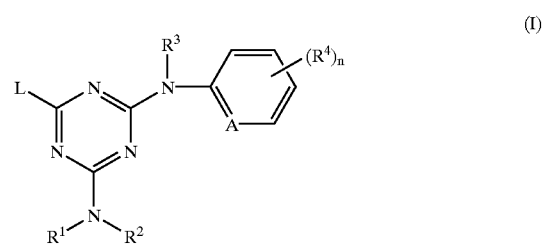

(I)

the N-oxides, the pharmaceutically acceptable addition salts and the stereochemically isomeric forms thereof, wherein A is CH, CR[4] or N; n is 0, 1, 2, 3 or 4; R[1] and R[2] are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted; or R[1] and R[2] taken together may form pyrrolidinyl, piperidinyl, morpholinyl, azido or mono- or di($C_{1-12}$alkyl)amino$C_{1-4}$alkylidene; R[3] is hydrogen, aryl, $C_{1-6}$alkylcarbonyl, optionally substituted $C_{1-6}$alkyl; and each R[4] independently is hydroxy, halo, $C_{1-6}$alkyl, $C_{1-6}$alkyloxy, cyano, aminocarbonyl, nitro, amino, trihalomethyl or trihalomethyloxy; L is —X—R[5] or —X—Alk—R[6]; wherein R[5] and R[6] each independently are indanyl, indolyl or phenyl; each of said indanyl, indolyl or phenyl may be substituted; and X is —NR[3]—, —NH—NH—, —N=N—, —O—, —S—, —S(=O)— or —S(=O)$_2$—; aryl is optionally substituted phenyl; Het is an optionally substituted aliphatic or aromatic heterocyclic radical; for the manufacture of a medicine for the treatment of subjects suffering from HIV (Human Immunodeficiency Virus) infection. It further relates to new compounds being a subgroup of the compounds of formula (I), their preparation and pharmaceutical compositions comprising them.

1 Claim, No Drawings

OTHER PUBLICATIONS

Patwa et al., Chem Abstract 84:105546v, (1976).
Mehta et al., Chem Abstract 91:157693e, (1976).
Winter et al., Chem Abstract 76:153794f (1972).
Goghari et al., Chem Abstract 88:146702u, (1978).
Borg–Warner Corp., Chem Abstract 91:141684s, (1979).
Borg–Warner Corp., Chem Abstract 91:124478k, (1979).
LaBrecque et al., Chem Abstract., 70:27953v, (1969).
Kreutzberger et al., Chem Abstract 105:226494n, (1986).
Shaihla et al., Chem Abstract 110:192772n, (1989).
Goghari et al., Chem Abstract 85:32961k, (1976).
Pathe et al., Chem Abstract 97:216130t, (1982).
Mehta et al., CHem Abstract 107:39759g, (1987).
Mehta et al., Chem Abstract 109:210966q, (1988).
Kandar et al., Chem Abstract 108:131655p, (1988).
Rajnani et al., Chem Abstract 86:189869e, (9177).
Rajnani et al., Chem Abstract 88:37757v, (1978).
Pandya etal., Chem Abstract 95:115471h, (1981).
Lina et al., Chem Abstract 109:6485c, (1988).
Pandya et al., Chem Abstract 85:32957p, (1976).
Freiberg et al., Chem Abstract 104:68822r, (1986).
Wakabayashi et al., Chem Abstract 73:108869m (1970).
Inoue et al., Chem Abstract 90:121520m, (1979).
Prakesh et al., Chem Abstract 113:112178x, (1990).
Zerkowski et al., Chem Abstract 114:5720a, (1990).
Zerkowski et al., Chem Abstract 120:285659c, (1994).
Folkers et al., Chem Abstract 117:158165, (1992).
Zerkowski et al., Chem Abstract 121:218199k, (1994).
Zerkowski et al., Chem Abstract 127:154844f, (1997).
Tyagi etal., Chem Abstract 115:49632q, (1990).
Hungarian Novelty Search Report, dated Nov. 14, 2002, for Hungarian Appln. No. P0101372.

* cited by examiner

TRISUBSTITUTED 1,3,5-TRIAZINE DERIVATIVES

This is a division of application Ser. No. 09/634,340, filed Aug. 8, 2000, which is a division of application Ser. No. 09/276,362, filed Mar. 25, 1999, now issued as U.S. Pat. No. 6,150,360 which claims benefit of application Ser. No. 60/079,633 filed Mar. 27, 1998.

The present invention is concerned with trisubstituted 1,3,5-triazine derivatives having HIV replication inhibiting properties. The invention further relates to methods for their preparation and pharmaceutical compositions comprising them. The invention also relates to the use of said compounds in the manufacture of a medicament useful for the treatment of subjects suffering from HIV (Human Immunodeficiency Virus) infection.

Substituted 1,3,5-triazines are disclosed in the prior art. For instance, Zerkowski et al. in Chem. Mater. (1994), 6(8), 1250–1257 discloses 4-[[4-amino-6-[(4-iodophenyl) amino]-1,3,5-triazin-2-yl]amino]benzonitrile and is used in the study of the crystal structure of H-bonded complexes. U.S. Pat. No. 2,671,810 discloses 4-cyano-anilino substituted 1,3,5-triazines useful as plasticizers, surface-active agents and as parfume ingredients. Brit. 701,789 discloses a process for preparing 4-cyano-anilino substituted 1,3,5-triazines.

Unexpectedly, it has now been found that the compounds of formula (I) effectively inhibit the replication of the Human Immunodeficiency Virus (HIV) and consequently may be useful for the treatment of individuals infected by HIV.

The present invention concerns the use of the compounds of formula

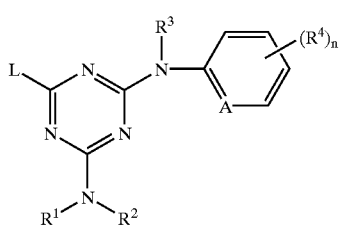

(I)

the N-oxides, the pharmaceutically acceptable addition salts and the stereochemically isomeric forms thereof, wherein
A is CH, $CR^4$ or N;
n is 0, 1, 2, 3 or 4;
$R^1$ and $R^2$ are each independently selected from hydrogen, hydroxy, $C_{1-12}$alkyl, $C_{1-12}$alkyloxy, $C_{1-12}$alkylcarbonyl, $C_{1-12}$alkyloxycarbonyl, aryl, amino, mono- or di($C_{1-12}$ alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$ alkyl)amino, aryl and Het; or
$R^1$ and $R^2$ taken together may form pyrrolidinyl, piperidinyl, morpholinyl, azido or mono- or di($C_{1-12}$alkyl)amino$C_{1-4}$ alkylidene;
$R^3$ is hydrogen, aryl, $C_{1-6}$alkylcarbonyl, $C_{1-6}$alkyl, $C_{1-6}$alkyloxycarbonyl, $C_{1-6}$alkyl substituted with $C_{1-6}$alkyloxycarbonyl; and
each $R^4$ independently is hydroxy, halo, $C_{1-6}$alkyl, $C_{1-6}$alkyloxy, cyano, aminocarbonyl, nitro, amino, trihalomethyl or trihalomethyloxy;

L is —X—$R^5$ or —X—Alk—$R^6$; wherein
$R^5$ and $R^6$ each independently are indanyl, indolyl or phenyl; each of said indanyl, indolyl or phenyl may be substituted with one, two, three, four or five substituents each independently selected from halo, $C_{1-6}$alkyl, $C_{1-6}$alkyloxy, hydroxy, $C_{1-6}$alkylcarbonyl, $C_{1-6}$alkyloxycarbonyl, formyl, cyano, nitro, amino and trifluoromethyl; and
X is —$NR^3$—, —NH—NH—, —N═N—, —O—, —S—, —S(═O)— or —S(═O)$_2$—;
Alk is $C_{1-4}$alkanediyl;
aryl is phenyl or phenyl substituted with one, two, three, four or five substituents each independently selected from halo, $C_{1-6}$alkyl, $C_{1-6}$alkyloxy, cyano, nitro and trifluoromethyl;
Het is an aliphatic or aromatic heterocyclic radical; said aliphatic heterocyclic radical is selected from pyrrolidinyl, piperidinyl, homopiperidinyl, piperazinyl, morpholinyl, tetrahydrofuranyl and tetrahydrothienyl wherein each of said aliphatic heterocyclic radical may optionally be substituted with an oxo group; and said aromatic heterocyclic radical is selected from pyrrolyl, furanyl, thienyl, pyridinyl, pyrimidinyl, pyrazinyl and pyridazinyl wherein each of said aromatic heterocyclic radical may optionally be substituted with hydroxy;
for the manufacture of a medicine for the treatment of subjects suffering from HIV (Human Immunodeficiency Virus) infection.

The present invention also relates to a method for treating warm-blooded animals suffering from HIV (Human Immunodeficiency Virus) infection. Said method comprises the administration of a therapeutically effective amount of a compound of formula (I) or a N-oxide form, a pharmaceutically acceptable addition salt or a stereochemically isomeric form thereof in admixture with a pharmaceutical carrier.

A particular embodiment of the present invention relates to compounds of formula

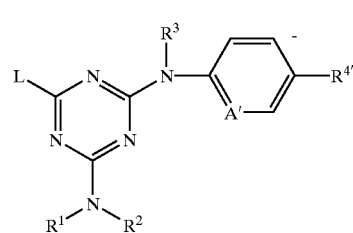

(I')

wherein
the variables $R^1$, $R^2$, $R^3$ and L are as defined in formula (I); and
A' is CH or N;
$R^{4'}$ is cyano, aminocarbonyl, nitro or trifluoromethyl;
with the proviso that
when $R^{4'}$ is cyano, $R^3$ is hydrogen, L is —X—$R^5$ wherein X is NH and $R^5$ is 4-cyanophenyl or 4-iodophenyl, then $NR^1R^2$ is other than $NH_2$, $NH[CH_2CH_2N(C_2H_5)_2]$, $N(C_2H_5)_2$, $NHCH_3$, $NHC_2H_5$ or NH(4-cyano-phenyl);
when $R^{4'}$ is trifluoromethyl, $R^3$ is hydrogen, L is —X—$R^5$ wherein X is NH and $R^5$ is 4-trifluoromethylphenyl, then $NR^1R^2$ is other than $NH_2$ or $N[(CH_2)_6CH_3]_2$;
when $R^{4'}$ is nitro, $R^3$ is hydrogen or methyl, L is —X—$R^5$ wherein X is NH or N—$CH_3$ and $R^5$ is 4-fluorophenyl, 2,6-dimethylphenyl, 4-methylphenyl or 4-nitrophenyl, then $NR^1R^2$ is other than NHaryl, $NCH_3$aryl, $N(aryl)_2$, $NH_2$, $NH[CH_2CH_2N(C_2H_5)_2]$, $NH[CH_2CH_2N(CH_3)_2]$, $NH[CH_2C(=O)OC_2H_5]$, $NH[CH_2C(=O)OH]$ or $N(C_2H_5)_2$;
when $R^{4'}$ is nitro, $R^3$ is hydrogen, L is —X—$R^5$ wherein X is $S(O)_2$ or S and $R^5$ is phenyl or 4-chlorophenyl, then $R^1$ and $R^2$ are other than aryl or $C_{1-12}$alkyl substituted with one or more carboxyl groups;
the N-oxides, the pharmaceutically acceptable addition salts and the stereochemically isomeric forms thereof.

As used in the foregoing definitions and hereinafter halo defines fluoro, chloro, bromo and iodo; $C_{1-4}$alkyl as a group or part of a group encompasses the straight and branched chained saturated hydrocarbon radicals having from 1 to 4 carbon atoms such as, for example, methyl, ethyl, propyl, butyl and the like; $C_{1-6}$alkyl as a group or part of a group encompasses the straight and branched chained saturated hydrocarbon radicals as defined in $C_{1-4}$alkyl as well as the higher homologues thereof containing 5 or 6 carbon atoms such as, for example pentyl or hexyl; $C_{1-12}$alkyl as a group or part of a group encompasses the straight and branched chained saturated hydrocarbon radicals as defined in $C_{1-6}$alkyl as well as the higher homologues thereof containing 7 to 10 carbon atoms such as, for example, heptyl, octyl, nonyl or decyl; $C_{1-12}$alkyl as a group or part of a group encompasses the straight and branched chained saturated hydrocarbon radicals as defined in $C_{1-10}$alkyl as well as the higher homologues thereof containing 11 or 12 carbon atoms such as, for example, undecyl, dodecyl and the like; $C_{1-4}$alkylidene as a group or part of a group defines geminal bivalent straight and branched chained hydrocarbons having from 1 to 4 carbon atoms such as, for example, methylene, ethylidene, propylidene, butylidene and the like; $C_{1-4}$alkanediyl as a group or part of a group encompasses those radicals defined under $C_{1-4}$alkylidene as well as other bivalent straight and branched chained hydrocarbons having from 1 to 4 carbon atoms such as, for example, 1,2-ethanediyl, 1,3-propanediyl, 1,4-butanediyl and the like.

When $R^5$ is optionally substituted indanyl or indolyl, it is preferably attached to the remainder of the molecule via the fused phenyl ring. For instance, $R^5$ is suitably 4-, 5-, 6- or 7-indolyl.

As used herein before, the term (=O) forms a carbonyl moiety when attached to a carbon atom.

When any variable (e.g. aryl, $R^3$, $R^4$ etc.) occurs more than one time in any constituent, each definition is independent.

Lines drawn into ring systems from substituents indicate that the bond may be attached to any of the suitable ring atoms. For instance, $R^4$ can be attached to any available carbon atom of the phenyl or pyridyl ring.

The pharmaceutically acceptable addition salts as mentioned hereinabove are meant to comprise the therapeutically active non-toxic acid addition salt forms which the compounds of formula (I) or (I') are able to form. The compounds of formula (I) or (I') which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term addition salts also comprises the hydrates and the solvent addition forms which the compounds of formula (I) or (I') are able to form. Examples of such forms are e.g. hydrates, alcoholates and the like.

The term stereochemically isomeric forms of compounds of formula (I) or (I'), as used hereinbefore, defines all possible compounds made up of the same atoms bonded by the same sequence of bonds but having different three-dimensional structures which are not interchangeable, which the compounds of formula (I) or (I') may possess. Unless other-wise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) or (I') both in pure form or in admixture with each other are intended to be embraced within the scope of the present invention.

Some of the compounds of formula (I) or (I') may also exist in their tautomeric forms. Such forms although not explicitly indicated in the above formula are intended to be included within the scope of the present invention.

Whenever used hereinafter, the term "compounds of formula (1)" or "compounds of formula (I)" is meant to include also their N-oxides, their pharmaceutically acceptable acid addition salts and all their stereoisomeric forms.

Suitably, L is —X—$R^5$ wherein $R^5$ is phenyl or phenyl substituted with one, two, three, four or five substituents each independently selected from halo, $C_{1-6}$alkyl, $C_{1-6}$alkyloxy, cyano, $C_{1-6}$alkylcarbonyl, nitro and trifluoromethyl.

Also suitable compounds are those compounds of the present invention wherein $R^5$ and $R^6$ are indanyl or indolyl both optionally substituted with 1, 2, 3, 4 or 5 substituents each independently selected from halo, $C_{1-6}$alkyl, $C_{1-6}$alkyloxy, hydroxy, $C_{1-6}$alkyl-carbonyl, $C_{1-6}$alkyloxycarbonyl, formyl, cyano, nitro, amino and trifluoromethyl; or $R^5$ and $R^6$ are phenyl substituted with 1, 2, 3, 4 or 5 substituents each independently selected from halo, $C_{1-6}$alkyl, $C_{1-6}$alkyloxy, hydroxy, $C_{1-6}$alkylcarbonyl, $C_{1-6}$alkyloxy-carbonyl, formyl, cyano, nitro, amino and trifluoromethyl whereby at least one of the substituents is in the ortho position relative to —X— or —X—Alk—.

In particular, L is 2,3,4,5,6-pentachloro-phenoxy, 2,3,5,6-tetrafluoro-4-hydroxy-phenoxy, 2,3,6-trichloro-phenoxy, 2,4,6-tribromo-3,5-dimethyl-phenoxy, 2,4,6-tribromo-phenoxy, 2,4,6-trichloro-phenoxy, 2,4,6-trifluoro-phenoxy, 2,4,6-trimethyl-phenoxy, 2,4-dichloro-3,5,6-trimethyl-phenoxy, 2,4-dichloro-6-methyl-phenoxy, 2,4-dichloro-phenoxy, 2,4-dimethyl-phenoxy, 2,5-dimethyl-phenoxy, 2,6-dibromo-4-chloro-3,5-dimethyl-phenoxy, 2,6-dibromo-4-methyl-phenoxy, 2,6-dichloro-4-fluoro-phenoxy, 2,6-dichloro-phenoxy, 2,6-dimethoxy-phenoxy, 2,6-dimethyl-4-nitro-phenoxy, 2,6-dimethyl-phenoxy, 2-acetyl-4,6-dichloro-phenoxy, 2-acetyl-4,6-difluoro-phenoxy, 2-amino-4,6-dichloro-5-methyl-phenoxy, 4-acetyl-2,6-dimethyl-phenoxy, 4-amino-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-cyano-2-methoxy-phenoxy, 4-formyl-2,6-dimethyl-phenoxy, 4-iodo-2,6-dimethyl-phenoxy, 2,3,4,5,6-pentafluoro-anilino, 2,3,4-trimethoxy-6-(methyloxycarbonyl)-anilino, 2,4,6-tribromo-anilino, 2,4,6-trichloro-anilino, 2,4,6-trimethoxy-anilino, 2,4,6-trimethyl-anilino, 2,4-dichloro-6-methyl-anilino, 2,4-dichloro-6-trifluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-diethylanilino, 2,6-dimethyl-anilino, 2-acetyl-5-methyl-anilino, 2-bromo-4,6-difluoro-anilino, 2-chloro-4,6-dimethyl-anilino, 2-chloro-4-fluoro-5-methyl-anilino, 2-chloro-6-methyl-anilino, 2-ethyl-6-methyl-anilino, 2-isopropyl-6-methyl-anilino, 3-amino-2,4,6-trimethyl-anilino, 3-bromo-2,4,6-trimethyl-anilino, 3-chloro-2,6-dimethyl-anilino, 4-bromo-2,6-diethyl-anilino, 4-bromo-2,6-dimethyl-anilino, 4-bromo-2-chloro-6-methyl-anilino, 4-methyl-anilino, N-methyl-2,4,6-trimethyl-anilino, 2,4,5-trichloro-phenylthio, 2,4,6-trimethyl-phenylthio, 2,4-dichloro-phenylthio, 2,4-difluoro-phenylthio, 2,4-dimethyl-phenylthio, 2,6-dichloro-phenylthio, 2-chloro-4-fluoro-phenylthio, 2,4,6-trichloro-phenylhydrazinyl, 2,6-dichloro-phenylhydrazinyl, 2,4-dichloro-6-methyl-benzylamino, 2,4-dimethoxy-benzylamino, indol-4-yl-oxy, or 5-acetyl-7-methyl-indan-4-yl-oxy;

more in particular, L is 2,3,4,5,6-pentachloro-phenoxy, 2,3,6-trichloro-phenoxy, 2,4,6-tribromo-3,5-dimethyl-phenoxy, 2,4,6-tribromo-phenoxy, 2,4,6-trichloro-phenoxy, 2,4,6-trifluoro-phenoxy, 2,4,6-trimethyl-phenoxy, 2,4-dichloro-3,5,6-tri-methyl-phenoxy, 2,4-dichloro-6-methyl-phenoxy, 2,4-dichloro-phenoxy, 2,4-dimethyl-phenoxy, 2,5-dimethyl-phenoxy, 2,6-dibromo-4-chloro-3,5-dimethyl-phenoxy, 2,6-di-bromo-4-methyl-phenoxy, 2,6-dichloro-4-fluoro-phenoxy, 2,6-dichloro-phenoxy, 2,6-dimethoxy-phenoxy, 2,6-dimethyl-4-nitro-phenoxy, 2,6-dimethyl-phenoxy, 2-acetyl-4,6-difluoro-phenoxy, 4-acetyl-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-cyano-2-methoxy-phenoxy, 4-formyl-2,6-dimethyl-phenoxy, 4-iodo-2,6-dimethyl-phenoxy, 2,4,6-tribromo-anilino, 2,4,6-trichloro-anilino, 2,4,6-trimethoxy-anilino, 2,4,6-trimethyl-anilino, 2,4-dichloro-6-methyl-anilino, 2,4-dichloro-6-trifluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-di-ethyl-anilino, 2,6-dimethyl-anilino, 2-bromo-4,6-difluoro-anilino, 2-chloro-4,6-di-methyl-anilino, 2-chloro-4-fluoro-5-methyl-anilino, 2-chloro-6-methyl-anilino, 2-ethyl-6-methyl-anilino, 3-amino-2,4,6-trimethyl-anilino, 3-bromo-2,4,6-trimethyl-anilino, 3-chloro-2,6-dimethyl-anilino, 4-bromo-2,6-diethyl-anilino, 4-bromo-2,6-dimethyl-anilino, 4-bromo-2-chloro-6-methyl-anilino, N-methyl-2,4,6-trimethyl-anilino, 2,4,5-trichloro-phenylthio, 2,4,6-trimethyl-phenylthio, 2,4-dichloro-phenylthio, 2,4-difluoro-phenylthio, 2,4-dimethyl-phenylthio, 2,6-dichloro-phenylthio, 2-chloro-4-fluoro-phenylthio, 2,4,6-trichloro-phenylhydrazinyl, 2,6-dichloro-phenylhydrazinyl, 2,4-dichloro-6-methyl-benzylamino or 5-acetyl-7-methyl-indan-4-yl-oxy;

preferably, L is 2,3,6-trichloro-phenoxy, 2,4,6-tribromo-3,5-dimethyl-phenoxy, 2,4,6-trichloro-phenoxy, 2,4,6-trifluoro-phenoxy, 2,4,6-trimethyl-phenoxy, 2,4-di-chloro-6-methyl-phenoxy, 2,4-dichloro-phenoxy, 2,4-dimethyl-phenoxy, 2,5-dimethyl-phenoxy, 2,6-dibromo-4-methyl-phenoxy, 2,6-dichloro-4-fluoro-phenoxy, 2,6-dichloro-phenoxy, 2,6-dimethyl-4-nitro-phenoxy, 2,6-dimethyl-phenoxy, 4-acetyl-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-formyl-2,6-di-methyl-phenoxy, 4-iodo-2,6-dimethyl-phenoxy, 2,4,6-tribromo-anilino, 2,4,6-trichloro-anilino, 2,4,6-trimethyl-anilino, 2,4-dichloro-6-methyl-anilino, 2,4-dichloro-6-tri fluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-dimethyl-anilino, 2-bromo-4,6-difluoro-anilino, 2-chloro-4,6-dimethyl-anilino, 2-chloro-6-methyl-anilino, 2-ethyl-6-methyl-anilino, 3-amino-2,4,6-trimethyl-anilino, 3-bromo-2,4,6-tri-methyl-anilino, 3-chloro-2,6-dimethyl-anilino, 4-bromo-2,6-dimethyl-anilino, 4-bromo-2-chloro-6-methyl-anilino, N-methyl-2,4,6-trimethyl-anilino, 2,4,5-trichloro-phenylthio, 2,4,6-trimethyl-phenylthio, 2,4-dichloro-phenylthio, 2,4-dimethyl-phenylthio, 2,6-di-chloro-phenylthio, 2-chloro-4-fluoro-phenylthio, 2,4,6-trichloro-phenylhydrazinyl, 2,6-dichloro-phenylhydrazinyl, 2,4-dichloro-6-methyl-benzylamino or 5-acetyl-7-methyl-indan-4-yl-oxy.

Of particular interest are the compounds of formula (I) or (I') wherein L is —X—$R^5$.

A special group of compounds are those compounds of formula (I') wherein $R^{4'}$ is cyano, L is —X—$R^5$ and $R^5$ is other than 4-cyanophenyl or 4-iodophenyl, in particular, $R^5$ is phenyl substituted with two, three, four or five substituents each independently selected from halo, $C_{1-6}$alkyl, $C_{1-6}$alkyloxy, hydroxy, $C_{1-6}$alkylcarbonyl, $C_{1-6}$alkyloxy carbonyl, formyl, cyano, nitro, amino and trifluoromethyl.

Another special group of compounds are those compounds of formula (I') wherein $R^{4'}$ is aminocarbonyl.

Also special compounds are those compounds of formula (I') wherein A' is CH.

Yet other special compounds are those compounds of formula (I') wherein L is —X—$R^5$ wherein X is —$NR^3$—, —NH—NH—, —N=N— or —O— and $R^5$ is indanyl, indolyl or phenyl; each of said indanyl, indolyl or phenyl may be substituted with two, three, four or five substituents each independently selected from halo, $C_{1-6}$alkyl, $C_{1-6}$alkyloxy, hydroxy, $C_{1-6}$alkylcarbonyl, $C_{1-6}$alkyloxycarbonyl, formyl, cyano, nitro, amino and trifluoro-methyl.

Still other special compounds are those compounds of formula (I') wherein $R^{4'}$ is cyano and L is —X—Alk—$R^6$.

Suitable compounds are those compounds of formula (I') wherein $R^4$ is aminocarbonyl, trifluoromethyl or cyano and L is 2,3,4,5,6-pentachloro-phenoxy, 2,3,5,6-tetrafluoro-4-hydroxy-phenoxy, 2,3,6-trichloro-phenoxy, 2,4,6-tribromo-3,5-dimethyl-phenoxy, 2,4,6-tribromo-phenoxy, 2,4,6-trichloro-phenoxy, 2,4,6-trifluoro-phenoxy, 2,4,6-trimethyl-phenoxy, 2,4-dichloro-3,5,6-trimethyl-phenoxy, 2,4-dichloro-6-methyl-phenoxy, 2,4-dichloro-phenoxy, 2,4-dimethyl-phenoxy, 2,5-dimethyl-phenoxy, 2,6-dibromo-4-chloro-3,5-dimethyl-phenoxy, 2,6-dibromo-4-methyl-phenoxy, 2,6-dichloro-4-fluoro-phenoxy, 2,6-dichloro-phenoxy, 2,6-dimethoxy-phenoxy, 2,6-dimethyl-4-nitro-phenoxy, 2,6-dimethyl-phenoxy, 2-acetyl-4,6-dichloro-phenoxy, 2-acetyl-4,6-difluoro-phenoxy, 2-amino-4,6-dichloro-5-methyl-phenoxy, 4-acetyl-2,6-dimethyl-phenoxy, 4-amino-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-cyano-2-methoxy-phenoxy, 4-formyl-2,6-dimethyl-phenoxy, 4-iodo-2,6-dimethyl-phenoxy, 2,3,4,5,6-pentafluoro-anilino, 2,3,4-trimethoxy-6-(methyloxycarbonyl)-anilino, 2,4,6-tribromo-anilino, 2,4,6-trichloro-anilino, 2,4,6-trimethoxy-anilino, 2,4,6-trimethyl-anilino, 2,4-dichloro-6-methyl-anilino, 2,4-dichloro-6-trifluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-diethyl-anilino, 2,6-dimethyl-anilino, 2-acetyl-5-methyl-anilino, 2-bromo-4,6-difluoro-anilino, 2-chloro-4,6-dimethyl-anilino, 2-chloro-4-fluoro-5-methyl-anilino, 2-chloro-6-methyl-anilino, 2-ethyl-6-methylanilino, 2-isopropyl-6-methyl-anilino, 3-amino-2,4,6-trimethyl-anilino, 3-bromo-2,4,6-trimethyl-anilino, 3-chloro-2,6-dimethyl-anilino, 4-bromo-2,6-diethyl-anilino, 4-bromo-2,6-di-methyl-anilino, 4-bromo-2-chloro-6-methyl-anilino, 4-methyl-anilino, N-methyl-2,4,6-trimethyl-anilino, 2,4,5-trichloro-phenylthio, 2,4,6-trimethyl-phenylthio, 2,4-dichloro-phenylthio, 2,4-difluoro-phenylthio, 2,4-dimethyl-phenylthio, 2,6-dichloro-phenylthio, 2-chloro-4-fluoro-phenylthio, 2,4,6-trichloro-phenylhydrazinyl, 2,6-dichloro-phenyl-hydrazinyl, 2,4-dichloro-6-methyl-benzylamino, 2,4-dimethoxy-benzylamino, indol-4-yl-oxy, or 5-acetyl-7-methyl-indan-4-yl-oxy.

Other suitable compounds are those compounds of formula (I') wherein $R^{4'}$ is nitro and L is 2,3,4,5,6-pentachloro-phenoxy, 2,3,5,6-tetrafluoro-4-hydroxy-phenoxy, 2,3,6-trichloro-phenoxy, 2,4,6-tribromo-3,5-dimethyl-phenoxy, 2,4,6-tribromo-phenoxy, 2,4,6-trichloro-phenoxy, 2,4,6-trifluoro-phenoxy, 2,4,6-trimethyl-phenoxy, 2,4-di-chloro-3,5,6-trimethyl-phenoxy, 2,4-dichloro-6-methyl-phenoxy, 2,4-dichloro-phenoxy, 2,4-dimethyl-phenoxy, 2,5-dimethyl-phenoxy, 2,6-dibromo-4-chloro-3,5-dimethyl-phenoxy, 2,6-dibromo-4-methyl-phenoxy, 2,6-dichloro-4-fluoro-phenoxy, 2,6-dichloro-phenoxy, 2,6-dimethoxy-phenoxy, 2,6-dimethyl-4-nitro-phenoxy, 2,6-dimethyl-phenoxy, 2-acetyl-4,6-dichloro-phenoxy, 2-acetyl-4,6-difluoro-phenoxy, 2-amino-4,6-dichloro-5-methyl-phenoxy, 4-acetyl-2,6-dimethyl-phenoxy, 4-amino-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-cyano-2-methoxy-phenoxy, 4-formyl-2,6-dimethyl-phenoxy, 4-iodo-2,6-dimethyl-phenoxy, 2,3,4,5,6-pentafluoro-anilino, 2,3,4-trimethoxy-6-(methyloxycarbonyl)-anilino, 2,4,6-tribromo-anilino, 2,4,6-trichloro-anilino, 2,4,6-trimethoxy-anilino, 2,4,6-trimethyl-anilino, 2,4-dichloro-6-methyl-anilino, 2,4-dichloro-6-trifluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-diethyl-anilino, 2-acetyl-5-methyl-anilino, 2-bromo-4,6-difluoro-anilino, 2-chloro-4,6-dimethyl-anilino, 2-chloro-4-fluoro-5-methyl-anilino, 2-chloro-6-methyl-anilino, 2-ethyl-6-methyl-anilino, 2-isopropyl-6-methyl-anilino, 3-amino-2,4,6-trimethyl-anilino, 3-bromo-2,4,6-trimethyl-anilino, 3-chloro-2,6-di-methyl-anilino, 4-bromo-2,6-diethyl-anilino, 4-bromo-2,6-dimethyl-anilino, 4-bromo-2-chloro-6-methyl-anilino, 4-methyl-anilino, N-methyl-2,4,6-trimethyl-anilino, 2,4,5-tri-chloro-phenylthio, 2,4,6-trimethyl-phenylthio, 2,4-dichloro-phenylthio, 2,4-difluoro-phenylthio, 2,4-dimethyl-phenylthio, 2,6-dichloro-phenylthio, 2-chloro-4-fluoro-phenylthio, 2,4,6-trichloro-phenylhydrazinyl, 2,6-dichloro-phenylhydrazinyl, 2,4-dichloro-6-methyl-benzylamino, 2,4-dimethoxy-benzylamino, indol-4-yl-oxy, or 5-acetyl-7-methyl-indan-4-yl-oxy.

Interesting groups of compounds are those groups of compounds of formula (D or (I') wherein one or more of the following conditions are met:

i. $R^1$ and $R^2$ are each independently selected from hydrogen, aryl or hydroxy; in particular, $R^1$ is hydrogen and $R^2$ is hydrogen or hydroxy;

ii. $R^3$ is hydrogen or $C_{1-6}$alkyl;

iii. L contains phenyl or phenyl substituted with one, two, three, four or five substituents, suitably two, three, four or five substituents, each independently selected from halo, hydroxy, $C_{1-6}$alkyl, $C_{1-6}$alkyloxy, $C_{1-6}$alkyloxycarbonyl, cyano, amino, trifluoromethyl, nitro, $C_{1-6}$alkylcarbonyl and formyl; and more in particular the substituents are selected from fluoro, bromo, chloro, cyano, methyl, ethyl, isopropyl and acetyl;

iv. $R^5$ or $R^6$ is indolyl, indanyl, phenyl, indanyl substituted with two or three substituents each independently selected from $C_{1-6}$alkyl and $C_{1-6}$alkylcarbonyl, or phenyl substituted with one, two, three, four or five substituents, suitably two, three, four or five substituents, each independently selected from halo, hydroxy, $C_{1-4}$alkyl, methyloxy, methyloxycarbonyl, cyano, amino, trifluoromethyl, nitro, methylcarbonyl and formyl;

v. X is —O—, —S—, —NR$^3$—, —NH—NH— or —N=N—; in particular, X is —O— or —NH— vi. Alk is methylene.

Other interesting compounds are those compounds of formula (I) wherein n is 1, A is CH and $R^4$ is cyano or aminocarbonyl; more in particular, $R^4$ is cyano substituted in the 4 position relative to the $NR^3$ moiety.

Still other interesting compounds are those compounds of formula (I) wherein $R^4$ is a halogen substituted in the 4 position relative to the NRS moiety, $R^1$ and $R^2$ are each independently selected from hydrogen, hydroxy, $C_{1-12}$alkyl, $C_{1-12}$alkyloxy, $C_{1-12}$alkyl-carbonyl, $C_{1-12}$alkyloxycarbonyl, amino, mono- or di($C_{1-12}$alkyl)amino, mono- or di($C_{1-12}$alkyl)aminocarbonyl wherein each of the aforementioned $C_{1-12}$alkyl groups may optionally and each individually be substituted with one or two substituents each independently selected from hydroxy, $C_{1-6}$alkyloxy, hydroxy$C_{1-6}$alkyloxy, carboxyl, $C_{1-6}$alkyloxycarbonyl, cyano, amino, imino, aminocarbonyl, aminocarbonylamino, mono- or di($C_{1-6}$alkyl)amino, aryl and Het; or $R^1$ and $R^2$ taken together may form pyrrolidinyl, piperidinyl, morpholinyl, azido or mono- or di($C_{12}$alkyl)amino-$C_{1-4}$alkylidene; and L is 2,3,4,5,6-pentachloro-phenoxy, 2,3,5,6-tetrafluoro-4-hydroxy-phenoxy, 2,3,6-trichloro-phenoxy, 2,4,6-tribromo-3,5-dimethyl-phenoxy, 2,4,6-tri-bromo-phenoxy, 2,4,6-trichloro-phenoxy, 2,4,6-trifluoro-phenoxy, 2,4,6-trimethyl-phenoxy, 2,4-dichloro-3,5,6-trimethyl-phenoxy, 2,4-dichloro-6-methyl-phenoxy, 2,4-dichloro-phenoxy, 2,4-dimethyl-phenoxy, 2,5-dimethyl-phenoxy, 2,6-dibromo-4-chloro-3,5-dimethyl-phenoxy, 2,6-dibromo-4-methyl-phenoxy, 2,6-dichloro-4-fluoro-phenoxy, 2,6-dichloro-phenoxy, 2,6-dimethoxy-phenoxy, 2,6-dimethyl-4-nitro-phenoxy, 2,6-dimethyl-phenoxy, 2-acetyl-4,6-dichloro-phenoxy, 2-acetyl-4,6-difluoro-phenoxy, 2-amino-4,6-dichloro-5-methyl-phenoxy, 4-acetyl-2,6-dimethyl-phenoxy, 4-amino-2,6-dimethyl-phenoxy, 4-bromo-2,6-dimethyl-phenoxy, 4-bromo-2-chloro-6-methyl-phenoxy, 4-chloro-2,3,6-trimethyl-phenoxy, 4-chloro-2,6-dimethyl-phenoxy, 4-cyano-2-methoxy-phenoxy, 4-formyl-2,6-dimethyl-phenoxy, 4-iodo-2,6-dimethyl-phenoxy, 2,3,4,5,6-pentafluoro-anilino, 2,3,4-trimethoxy-6-(methyloxycarbonyl)-anilino, 2,4,6-tribromo-anilino, 2,4,6-trichloro-anilino, 2,4,6-trimethoxy-anilino, 2,4,6-trimethyl-anilino, 2,4-dichloro-6-methyl-anilino, 2,4-dichloro-6-trifluoromethyl-anilino, 2,6-dibromo-4-isopropyl-anilino, 2,6-dibromo-4-methyl-anilino, 2,6-dichloro-4-trifluoromethyl-anilino, 2,6-dichloro-anilino, 2,6-diethyl-anilino, 2-acetyl-5-methyl-anilino, 2-bromo-4,6-difluoro-anilino, 2-chloro-4,6-dimethyl-anilino, 2-chloro-4-fluoro-5-methyl-anilino, 2-chloro-6-methyl-anilino, 2-ethyl-6-methyl-anilino, 2-isopropyl-6-methyl-anilino, 3-amino-2,4,6-trimethyl-anilino, 3-bromo-2,4,6-tri-methyl-anilino, 3-chloro-2,6-dimethyl-anilino, 4-bromo-2,6-diethyl-anilino, 4-bromo-2,6-dimethyl-anilino, 4-bromo-2-chloro-6-methylanilino, 4-methyl-anilino, N-methyl-2,4,6-trimethyl-anilino, 2,4,5-trichloro-phenylthio, 2,4,6-trimethyl-phenylthio, 2,4-di-chloro-phenylthio, 2,4-difluoro-phenylthio, 2,4-dimethyl-phenylthio, 2,6-dichloro-phenylthio, 2-chloro-4-fluoro-phenylthio, 2,4,6-trichloro-phenylhydrazinyl, 2,6-dichloro-phenylhydrazinyl, 2,4-dichloro-6-methyl-benzylamino, 2,4-dimethoxy-benzylamino, indol-4-yl-oxy, or 5-acetyl-7-methyl-indan-4-yl-oxy.

Particular compounds are those compounds of formula (1) or (I') wherein $R^1$ is hydrogen, $R^2$ is hydrogen, aryl or hydroxy, $R^3$ is hydrogen and X is —O— or —NH—.

Other particular compounds are those compounds of formula (D or (I') wherein $R^5$ or $R^6$ is a 2,4-disubstituted-, a 2,5-disubstituted-, a 2,6-disubstituted-, a 2,3,6-trisubstituted-, a 2,4,6-trisubstituted-, a 2,3,4,6-tetrasubstituted-, a 2,4,5,6-tetrasubstituted-or a 2,3,4,5,6-pentasubstituted phenyl group; in particular a 2,3,4,5,6-pentahalo, 2,3,5,6-tetrahalo-4-hydroxy-, 2,3,6-trihalo-, 2,4,5-trihalo-, 2,4,6-trihalo-3,5-di$C_{1-4}$alkyl-, 2,4,6-tri$C_{1-4}$alkyl-, 2,4,6-tri$C_{1-4}$alkyloxy, 2,4-dihalo-3,5,6-triC, 4alkyl-, 2,4-dihalo-6-$C_{1-4}$alkyl-, 2,4-dihalo-6-trifluoromethyl, 2,4-dihalo-, 2,4-di$C_{1-4}$alkyl-, 2,5-di$C_{1-4}$alkyl-, 2,6-dihalo-4-$C_{1-4}$alkyl-, 2,6-dihalo-4-$C_{1-4}$alkyl-, 2,6-dihalo-4-trifluoromethyl-, 2,6-dihalo-, 2,6-di$C_{1-4}$alkyloxy-, 2,6-di$C_{1-4}$alkyl-4-nitro-, 2,6-di$C_{1-4}$alkyl-, 2-acetyl-4,6-dihalo-, 2-acetyl-4,6-dihalo-, 2-acetyl-5-$C_{1-4}$alkyl-, 2-amino-4,6-dihalo-5-$C_{1-4}$alkyl-, 2-halo-4,6-di$C_{1-4}$alkyl-, 2,4-dihalo-5-$C_{1-4}$alkyl-, 2-halo-6-$C_{1-4}$alkyl-, 2,6-di$C_{1-4}$alkyl-, 3-amino-2,4,6-tri$C_{1-4}$alkyl-, 3-halo-2,4,6-tri$C_{1-4}$alkyl-, 3-halo-2,6-di$C_{1-4}$alkyl-, 4-acetyl-2,6-di$C_{1-4}$alkyl-, 4-amino-2,6-di$C_{1-4}$alkyl-, 4-halo-2,6-di$C_{1-4}$alkyl-, 4-halo-2,3,6-tri-$C_{1-4}$alkyl-, 4-cyano-2-$C_{1-4}$alkyloxy-, 4-formyl-2,6-di$C_{1-4}$alkyl-, 4-$C_{1-4}$alkyl- or a 2,3,4-tri$C_{1-4}$alkyloxy-6-($C_{1-4}$alkyloxycarbonyl)-phenyl group; more in particular, $R^5$ or $R^6$ is a 2,3,4,5,6-pentachloro-, 2,3,4,5,6-pentafluoro-, 2,3,5,6-tetrafluoro-4-hydroxy-, 2,3,6-tri-chloro-, 2,4,5-trichloro-, 2,4,6-tribromo-3,5-dimethyl-, 2,4,6-tribromo-, 2,4,6-trichloro-, 2,4,6-trifluoro-, 2,4,6-trimethyl-, 2,4,6-trimethoxy, 2,4-dichloro-3,5,6-trimethyl-, 2,4-dichloro-6-methyl-, 2,4-dichloro-6-trifluoromethyl, 2,4-dichloro-, 2,4-difluoro-, 2,4-dimethyl-, 2,5-dimethyl-, 2,6-dibromo-4-chloro-3,5-dimethyl-, 2,6-dibromo-4-isopropyl-, 2,6-dibromo-4-methyl-, 2,6-dichloro-4-trifluoromethyl-, 2,6-dichloro-4-fluoro-, 2,6-dichloro-, 2,6-dimethoxy-, 2,6-dimethyl-4-nitro-, 2,6-dimethyl-, 2,6-diethyl-, 2-acetyl-4,6-dichloro-, 2-acetyl-4,6-difluoro-, 2-acetyl-5-methyl-, 2-amino-4,6-dichloro-5-methyl-, 2-bromo-4,6-difluoro-, 2-chloro-4,6-dimethyl-, 2-chloro-4-fluoro-5-methyl-, 2-chloro-4-fluoro-, 2-chloro-6-methyl-, 2-ethyl-6-methyl-, 2-isopropyl-6-methyl-, 3-amino-2,4,6-trimethyl-, 3-bromo-2,4,6-trimethyl-, 3-chloro-2,6-dimethyl-, 4-acetyl-2,6-dimethyl-, 4-amino-2,6-dimethyl-, 4-bromo-2,6-diethyl-, 4-bromo-2,6-dimethyl-, 4-bromo-2-chloro-6-methyl-, 4-chloro-2,3,6-trimethyl-, 4-chloro-2,6-dimethyl-, 4-cyano-2-methoxy-, 4-formyl-2,6-dimethyl-, 4-iodo-2,6-dimethyl-, 4-methyl- or a 2,3,4-trimethoxy-6-(methyloxycarbonyl)-phenyl group.

Preferred compounds are those compounds of formula (I') wherein A' is CH, $R^{4'}$ is cyano, X is —O— or —NH— and $R^5$ or $R^6$ is phenyl substituted with two or three substituents each independently selected from halo, $C_{1-6}$alkyl, $C_{1-6}$alkylcarbonyl, formyl, nitro or cyano.

Most preferred are
4-[[4-amino-6-(2,6-dimethylphenoxy)-1,3,5-triazin-2-yl]amino]benzonitrile;
4-[[4-amino-6-[(2-chloro-6-methylphenyl)amino]-1,3,5-triazin-2-yl]amino]benzonitrile;
4-[[4-amino-6-[(2,4,6-trimethylphenyl)amino]-1,3,5-triazin-2-yl]amino]benzonitrile;
4-[[4-(hydroxyamino)-6-[(2,4,6-trimethylphenyl)amino]-1,3,5-triazin-2-yl]amino]-benzonitrile;
4-[[4-amino-6-[(2-ethyl-6-methylphenyl)amino]-1,3,5-triazin-2-yl]amino]benzonitrile;
4-[[4-amino-6-[(2,6-dichlorophenyl)thio]-1,3,5-triazin-2-yl]amino]benzonitrile;
4-[[4-(hydroxyamino)-6-[(2,4,6-trichlorophenyl)amino]-1,3,5-triazin-2-yl]amino]-benzonitrile;
4-[[4-amino-6-(2,4,6-trimethylphenoxy)-1,3,5-triazin-2-yl]amino]benzonitrile;
4-[[4-(hydroxyamino)-6-(2,4,6-trimethylphenoxy)-1,3,5-triazin-2-yl]amino]-benzonitrile;
4-[[4-amino-6-[(2,4-dichloro-6-methylphenyl)amino]-1,3,5-triazin-2-yl]amino]-benzonitrile;
4-[[4-[(2,4-dichloro-6-methylphenyl)amino]-6-(hydroxyamino)-1,3,5-triazin-2-yl]-amino]benzontrile;
4-[[4-(hydroxyamino)-6-(2,4,6-trichlorophenoxy)-1,3,5-triazin-2-yl]amino]benzonitrile trifluoroacetate (1:1);
4-[[4-(4-acetyl-2,6-dimethylphenoxy)-6-amino-1,3,5-triazin-2-yl]amino]benzonitrile;
4-[[4-amino-6-(2,4,6-tribromophenoxy)-1,3,5-triazin-2-yl]amino]benzonitrile;
4-[[4-amino-6-(4-nitro-2,6-dimethylphenoxy)-1,3,5-triazin-2-yl]amino]benzonitrile;
4-[[4-amino-6-(2,6-dibromo-4-methylphenoxy)-1,3,5-triazin-2-yl]amino]benzonitrile;
4-[[4-amino-6-(4-formyl-2,6-dimethylphenoxy)-1,3,5-triazin-2-yl]amino]benzonitrile;
4-[[4-amino-6-[(2,4-dichlorophenyl)thio]-1,3,5-triazin-2-yl]amino]benzonitrile;
4-[[4-[(5-acetyl-2,3-dihydro-7-methyl-1H-inden-4-yl)oxy]-6-amino-1,3,5-triazin-2-yl]-amino]benzonitrile;
4-[[4-amino-6-[(4-bromo-2-chloro-6-methylphenyl)amino]-1,3,5-triazin-2-yl]amino]-benzonitrile;
4-[[4-amino-6-[(2-chloro-4,6-dimethylphenyl)amino]-1,3,5-triazin-2-yl]amino]-benzonitrile;
4-[[4-amino-6-[[2,4-dichloro-6-(trifluoromethyl)phenyl]amino]-1,3,5-triazin-2-yl]-amino]benzonitrile;
4-[[4-amino-6-[methyl(2,4,6-trimethylphenyl)amino]-1,3,5-triazin-2-yl]amino]benzonitrile;
4-[[4-amino-6-[(2,6-dibromo-4-methylphenyl)amino]-1,3,5-triazin-2-yl]amino]-benzonitrile;
4-[[4-amino-6-[[2,6-dibromo-4-(1-methylethyl)phenyl]amino]-1,3,5-triazin-2-yl]-amino]benzonitrile; the N-oxides, the pharmaceutically acceptable addition salts and the stereochemically isomeric forms thereof.

The compounds of formula (I) can be prepared according to art-known procedures.

In particular, the compounds of formula (I') can be prepared by reacting an intermediate of formula (II) wherein $W^1$ is a suitable leaving group such as, for example, a halogen, with an amino derivative of formula (III) in a reaction inert solvent such as, for example, 1,4-dioxane, tetrahydrofuran, 2-propanol, N-methyl-pyrrolidinone and the like, optionally in the presence of a suitable base such as, for example, sodiumhydroxide, sodiumhydride, triethylamine or N,N-diisopropylethylamine or the like.

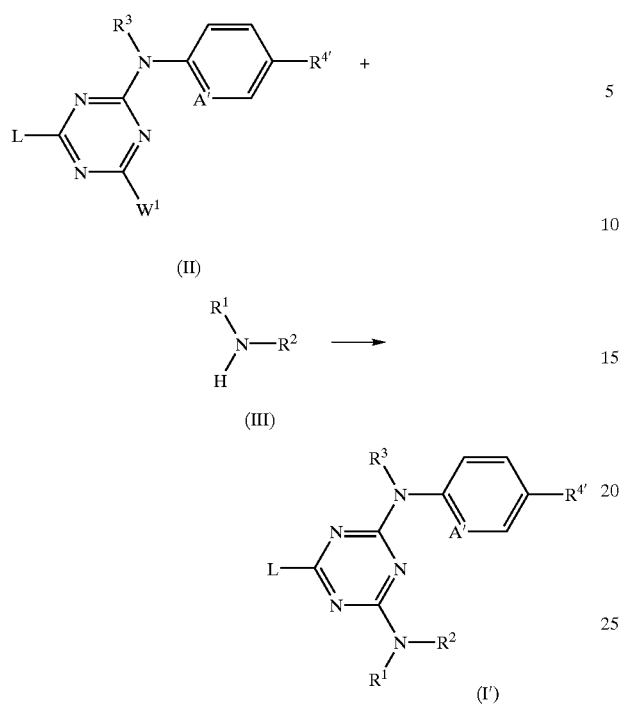

In this and the following preparations, the reaction products may be isolated from the reaction medium and, if necessary, further purified according to methodologies generally known in the art such as, for example, extraction, crystallization, distillation, trituration and chromatography.

In case $R^2$ contains a hydroxy moiety, it may be convenient to perform the above reaction with a protected form of intermediate (Im) whereby the hydroxy moiety bears a suitable protecting group P being, for instance, a trialkylsilyl group, and subsequently removing the protective group according to art-known methodologies.

The compounds of formula (I') can also conveniently be prepared using solid phase synthesis techniques. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample.

Suitable polymer supports include for instance Rink Amide resin (Calbiochem-Novabiochem Corp., San Diego, Calif.).

For instance, the compounds of formula (I') wherein $NR^1R^2$ is $NH^2$, said compounds being represented by formula (I'-a), were prepared according to the procedure depicted in Scheme 1.

Scheme 1

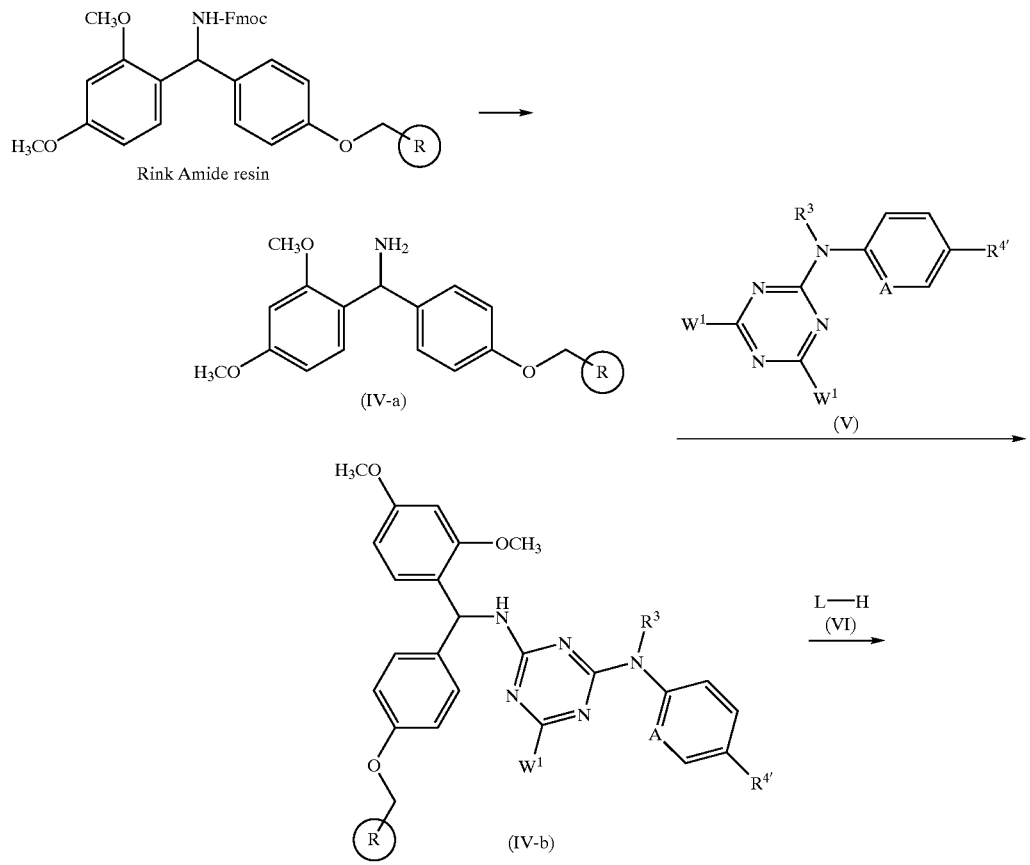

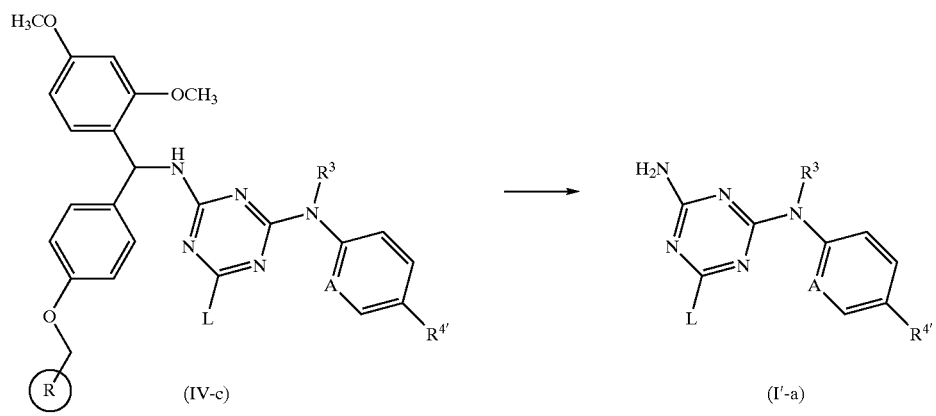

(IV-c) → (I'-a)

In scheme 1, Rink Amide resin is reacted in a suitable solvent such as, for example N,N-dimethylformamide in the presence of piperidine to obtain the primary amine of formula (IV-a) which can then further be reacted with an intermediate of formula (V) wherein WI is a suitable leaving group such as, for example, a halogen, in the presence of a base such as for example, N,N-diisopropylethylamine, in a suitable solvent such as, for example, dimethylsulfoxide. Impurities can be removed by washing numerous times with various solvents such as, for example, N,N-dimethylformamide, dichloro-methane, dimethylsulfoxide and the like. The resulting polymer-bound intermediate of formula (IV-b) was then further reacted with L—H (VI). To facilitate this transformation, silver triflate, sodium hexamnethyldisilazide or cesium carbonate may be used. The resin is finally treated with a cleavage reagent such as for example trifluoroacetic acid in tetrahydrofuran, thus obtaining compounds of formula (I') wherein $NR^1R^2$ is $NH_2$.

The compounds of formula (I') may further be prepared by converting compounds of formula (I') into each other according to art-known group transformation reactions.

The above specified reaction procedures for the preparation of compounds of formula (I') or subgroups thereof, can also be applied for the preparation of compounds of formula (I).

Some of the intermediates as mentioned hereinabove are commercially available or can be prepared according to art-known procedures. Of some, the preparation is described hereinbelow.

Intermediates of formula (II) can be prepared by reacting an intermediate of formula (VII) wherein $W^1$ is a suitable leaving group such as, for example, a halogen, with an amine derivative of formula (VIII) in a reaction-inert solvent such as, for example, tetrahydrofuran, 1,4-dioxane or the like, in the presence of a suitable base such as, for example, triethylamine; and subsequently reacting the thus obtained intermediate of formula (V) with an intermediate of formula (VI) in a reaction-inert solvent such as, for example, acetonitrile, 1,4-dioxane or the like, in the presence of a base such as, for example, potassium carbonate, sodium hydride, N,N-diisopropyl-ethylamine or the like.

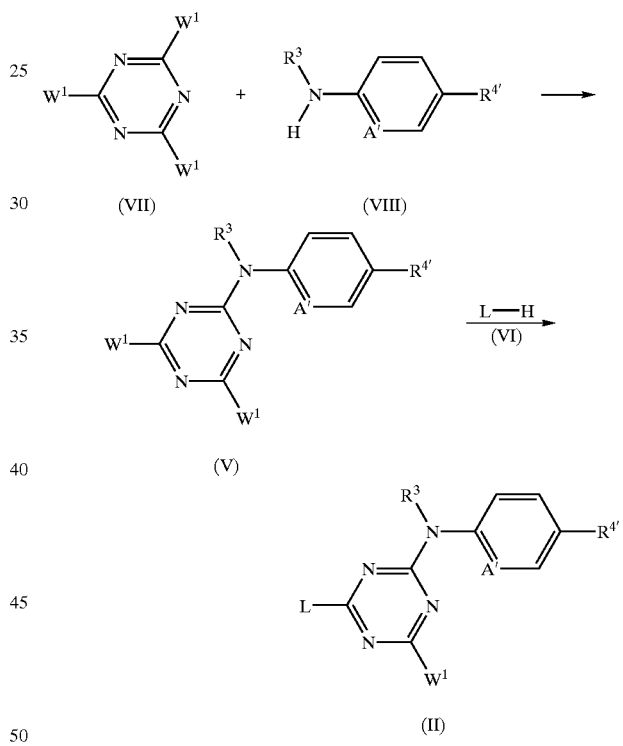

The order of the above reaction scheme may also be reversed, i.e. first an intermediate of formula (VII) may be reacted with an intermediate of formula (VI), and then, the resulting intermediate of formula (IX) may further be reacted with an amine derivative of formula (VIII); thus forming an intermediate of formula (II).

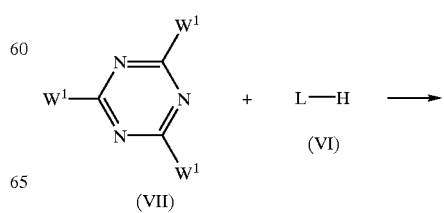

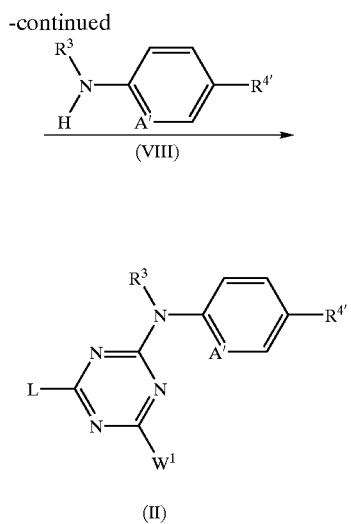

Particular intermediates are those intermediates of formula (II) wherein $R^{4'}$ is is as defined in the compounds of formula (I'), $R^3$ is hydrogen, A' is CH, $W^1$ is a halogen such as, chloro and bromo, and L is as defined in the compounds of formula (I) provided that $R^5$ is other than p-cyano-phenyl, p-nitro-phenyl, p-methoxy-phenyl and p-aminocarbonyl-phenyl, and $R^6$ is other than 2-(4-hydroxyphenyl)ethyl] amino; more in particular, $R^3$, A' and $W^1$ are as defined above, $R^4$ is cyano and L is —X—$R^5$ or —X—Alk—$R^6$; wherein $R^5$ and $R^6$ each independently are indanyl, indolyl or phenyl; each of said indanyl, indolyl or phenyl may be substituted with two, three, four or five substituents each independently selected from halo, $C_{1-6}$alkyl, $C_{1-6}$alkyloxy, hydroxy, $C_{1-6}$alkyl-carbonyl, $C_{1-6}$alkyloxycarbonyl, formyl, cyano, nitro, amino and trifluoromethyl.

Compounds of formula (I') and some of the intermediates may have one or more stereogenic centers in their structure, present in a R or a S configuration.

The compounds of formula (I') as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), (I') and the intermediates of formula (II) show antiretroviral properties, in particular against Human Immunodeficiency Virus (HIV), which is the aetiological agent of Acquired Immune Deficiency Syndrome (AIDS) in humans. The HIV virus preferentially infects human T-4 cells and destroys them or changes their normal function, particularly the coordination of the immune system. As a result, an infected patient has an everdecreasing number of T-4 cells, which moreover behave abnormally. Hence, the immunological defense system is unable to combat infections and neoplasms and the HIV infected subject usually dies by opportunistic infections such as pneumonia, or by cancers. Other conditions associated with HIV infection include thrombocytopaenia, Kaposi's sarcoma and infection of the central nervous system characterized by progressive demyelination, resulting in dementia and symptoms such as, progressive dysarthria, ataxia and disorientation. HIV infection further has also been associated with peripheral neuropathy, progressive generalized lymphadenopathy (PGL) and AIDS-related complex (ARC).

The present compounds also show activity against HIV-1 strains that have acquired resistance to art-known non-nucleoside reverse transcriptase inhibitors. They also have little or no binding affinity to human cc-I acid glycoprotein.

Due to their antiretroviral properties, particularly their anti-HIV properties, especially their anti-HIV-1-activity, the compounds of formula (I) or (I') or any subgroup thereof, their N-oxides, pharmaceutically acceptable salts and the stereochemically isomeric forms thereof, are useful in the treatment of individuals infected by HIV and for the prophylaxis of these individuals. In general, the compounds of the present invention may be useful in the treatment of warm-blooded animals infected with viruses whose existence is mediated by, or depends upon, the enzyme reverse transcriptase. Conditions which may be prevented or treated with the compounds of the present invention, especially conditions associated with HIV and other pathogenic retroviruses, include AIDS, AIDS-related complex (ARC), progressive generalized lymphadenopathy (PGL), as well as chronic CNS diseases caused by retroviruses, such as, for example HIV mediated dementia and multiple sclerosis.

The compounds of the present invention or any subgroup thereof, such as the compounds of formula (I'), may therefore be used as medicines against above-mentioned conditions. Said use as a medicine or method of treatment comprises the systemic administration to HIV-infected subjects of an amount effective to combat the conditions associated with HIV and other pathogenic retroviruses, especially HIV-1.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

It is especially advantageous to formulate the aforementioned pharmaceutical compositions in dosage unit form for ease of administration and uniformity of dosage. Dosage unit form as used herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions and the like, and segregated multiples thereof.

Those of skill in the treatment of HIV-infection could determine the effective daily amount from the test results presented here. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of an antiretroviral compound and a compound of formula (I) or (I') or any subgroup thereof can be used as a medicine. Thus, the present invention also relates to a product containing (a) a compound of formula (I) or (I') or any subgroup thereof, and (b) another antiretroviral compound, as a combined preparation for simultaneous, separate or sequential use in anti-HIV treatment. The different drugs may be combined in a single preparation together with pharmaceutically acceptable carriers. Said other antiretroviral compounds may be known antiretroviral compounds such as nucleoside reverse transcriptase inhibitors, e.g. zidovudine (3'-azido-3'-deoxythymidine, AZT), didanosine (dideoxy inosine; ddI), zalcitabine (dideoxycytidine, ddC) or lamivudine (3'-thia-2'-3'-dideoxycytidine, 3TC) and the like; non-nucleoside reverse transciptase inhibitors such as suramine, foscamet-sodium (trisodium phosphono formate), nevirapine (11-cyclopropyl-5,11-dihydro-4-methyl-6H-dipyrido[3,2-b:2', 3'-e][1,4]diazepin-6-one), sustiva (efavirenz), tacrine (tetrahydro-aminoacridine) and the like; compounds of the TIBO (tetrahydro-imidazo[4,5,1-jk][1,4]-benzodiazepine-2 (1H)-one and thione)-type e.g. (S)-8-chloro-4,5,6,7-tetrahydro-5-methyl-6-(3-methyl-2-butenyl)imidazo-[4,5,1-jk][1,4]benzodiazepine-2(1H)-thione; compounds of the α-APA (α-anilino phenyl acetamide) type e.g. α-[(2-nitrophenyl)amino]-2,6-dichlorobenzene-acetamide and the like; TAT-inhibitors, e.g. RO-5-3335 and the like; protease inhibitors e.g. indinavir, ritanovir, saquinovir and the like; NMDA receptor inhibitors e.g. pentamidine; α-glycosidase inhibitor e.g. castanospermine and the like; Rnase H inhibitor e.g. dextran (dextran sulfate) and the like; or immunomodulating agents, e.g. levamisole, thymopentin and the like.

The following examples are intended to illustrate the present invention.

Experimental Part

A) Preparation of the Intermediates

EXAMPLE A.1 a) 2,4,6-trichloro-1,3,5-triazine (0.07440 mol) and tetrahydrofuran (100 ml) were combined and cooled to −75° C. under Ar atmosphere. 4-aminobenzonitrile (0.07440 mol) was added and the solution was stirred for 4 hours at −75° C. Triethyl-amine (0.07440 mol) was added dropwise and the reaction mixture was allowed to warm up slowly to room temperature and stirred for 3 days. After adding 1,4-dioxane (100 ml), the resulting precipitate was collected by filtration, washed with tetrahydro-furan, and dried, yielding 12.74 g 4-[(4,6-dichloro-1,3,5-triazin-2-yl)amino]benzonitrile (interm. 1).

b) NaH (0.0113 mol), $CH_3CN$ (30 ml) and 2,6-dichlorophenol were combined and stirred for 15 minutes under Ar atmosphere. Then, intermediate (1) (0.0113 mol) was added and the reaction mixture was stirred at room temperature for 16 hours. The reaction mixture was quenched with ice water (30 ml) and filtered. A precipitate formed in the filtrate and was filtered off. The resulting solid was washed with $H_2O$ and $CH_3CN$, then dried, yielding 0.62 g (14%) of 4-[[4-chloro-6-(2,6-dichlorophenoxy)-1,3,5-triazin-2-yl]amino]benzonitrile (interm. 2).

c) N,N-Diisopropyl-ethylamine (0.00714 mol) was added to a solution of 2-chloro-6-methylbenzenamine (0.00714 mol) in 1,4-dioxane (20 ml) under Ar flow. A solution of intermediate (1) (0.00714 mol) in 1,4-dioxane (5 ml) was added. The reaction mixture was stirred and refluxed for 24 hours. The solvent was evaporated and $CH_2Cl_2$ was added. The organic layer was washed with a saturated aqueous $NaHCO_3$ solution, and the resulting precipitate was filtered off, yielding 0.56 g (21.1%) of 4-[[4-chloro-6-[(2-chloro-6-methylphenyl)amino]-1,3,5-triazin-2-yl] amino]benzonitrile (intern. 3).

EXAMPLE A.2 a) 2,4,6-trichloro-1,3,5-triazine (0.0266 mol) was added to 1,4-dioxane (50 ml) under Ar atmosphere. The solution was stirred until it became homogeneous, then 2,6-dichlorobenzenamine (0.0266 mol) and $K_2CO_3$ (0.0362 mol) were added. The reaction mixture was stirred at room temperature for 3 days. The solvent was evaporated. Water was added to the residue and the aqueous phase was extracted with $CH_2Cl_2$. The separated organic layer was washed with brine, dried with potassium carbonate, filtered and the filtrate was evaporated, yielding 7.52 g (91.2%) of N-(2,6-dichlorophenyl)-4,6-dichloro-1,3,5-triazin-2-amine (interm. 4).

b) 1,4-Dioxane (50 ml), 4-cyano-aniline (0.0243 mol), and N,N-diisopropyl-ethylamine (0.0243 mol) were added to intermediate (4) (0.0243 mol) under Ar atmosphere. The reaction mixture was stirred and refluxed for 1 week. The reaction was cooled, the solvent was evaporated and the residue was dissolved in ethyl acetate. The organic phase was washed with a saturated NaHCO₃ solution and with brine, dried with potassium carbonate, filtered, and the solvent was evaporated. The residue was stirred in a mixture of CH₂Cl₂ and saturated NaHCO₃, and the precipitate filtered off, yielding 2.26 g (23.8%) of 4-[[4-chloro-6-[(2,6-dichlorophenyl)amino]-1,3,5-triazin-2-yl]amino]benzonitrile (interm. 5).

EXAMPLE A.3

Rink Amide resin (15 g; Calbiochem-Novabiochem Corp., San Diego, Calif.; Product No. 01-64-0013) was washed in a reaction vessel with CH$_2$Cl$_2$ (100 ml), N,N-dimethylformamide (200 ml), and N,N-dimethylformamide:piperidine (150 ml:50 ml) was added. The mixture was agitated for 2 hours, washed with N,N-dimethyl-formamide, CH$_2$Cl$_2$, and dimethylsulfoxide. Intermediate (1) (0.06 mol), N,N-diiso-propylethylamine (10.5 ml) and dimethylsulfoxide (200 ml) were added and the reaction mixture was agitated for three days, then washed with N,N-dimethylformamide and CH$_2$Cl$_2$, yielding the resin bound intermediate (1).

Table 1 lists intermediates which were prepared according to one of the above examples.

B. Preparation of the Compounds of Formula (I')

EXAMPLE B.1 a) A mixture of intermediate (8) (0.00137 mol) and NH$_3$ in 1,4-dioxane (0.5 M; 0.00548 mol) was heated in a pressure vessel at 100° C. for 6 days. The solvent was evaporated and the residue was dissolved in CH$_2$Cl$_2$, washed with a saturated aqueous NaHCO$_3$ solution, dried, filtered and the solvent was evaporated. The residue was purified by column chromatography over silica gel (eluent: CH$_2$Cl$_2$/CH$_3$OH 100/0, 99/1 and 98/2). The desired fractions were collected and the solvent was evaporated. The residue was recrystallized from toluene. The precipitate was filtered off and dried, yielding 0.29 g (61.4%) of 4-[[4-amino-6-[(2,4,6-trimethylphenyl)amino]-1,3,5-triazin-2-yl]amino]benzonitrile (compound 9).

b) As an alternative for the preparation of compound (9), a mixture of intermediate (8) (0.0230 mol) in NH$_3$ in 2-propanol (2.0 M; 60 ml) and NH$_3$ in 1,4-dioxane (0.5 M; 20 ml) was heated at 95° C. for 21 hours. The solvent was evaporated. The residue was dissolved in ethyl acetate, washed with 1 N NaOH, water and brine, dried, filtered and the filtrate was evaporated. The residue was recrystallized with acetonitrile, yielding 5.25 g (66.1%) of compound (9).

c) Intermediate (21) (0.00150 mol) and 0.5 M NH$_3$ in 1,4-dioxane (0.015 mol) were added into a pressure flask. The reaction mixture was heated to 40° C. After 5 days, the reaction was cooled to room temperature. 2.0 M NH$_3$ in 2-propanol (0.015 mol) was added, and the reaction was returned to 40° C. The reaction was diluted with diethylether and extracted with cold 1 M NaOH. The aqueous layer was extracted twice more, and the organic

TABLE 1

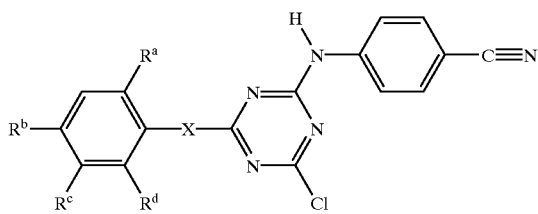

| Int. No. | Ex. No. | X | R$^a$ | R$^b$ | R$^c$ | R$^d$ | physical data |
|---|---|---|---|---|---|---|---|
| 2 | A1b | —O— | Cl | H | H | Cl | |
| 3 | A1c | —NH— | Cl | H | H | CH$_3$ | |
| 5 | A2b | —NH— | Cl | H | H | Cl | |
| 6 | A2b | —NH— | CH$_3$ | H | H | CH$_3$ | |
| 7 | A1c | —NH— | CH(CH$_3$)$_2$ | H | H | CH$_3$ | |
| 8 | A1c | —NH— | CH$_3$ | CH$_3$ | H | CH$_3$ | |
| 9 | A1c | —NH— | C$_2$H$_5$ | H | H | C$_2$H$_5$ | |
| 10 | A1c | —NH— | C(=O)CH$_3$ | H | CH$_3$ | H | |
| 11 | A1c | —NH— | CH$_3$ | Br | H | CH$_3$ | |
| 12 | A1c | —NH— | CH$_3$ | CH$_3$ | Br | CH$_3$ | |
| 13 | A1c | —NH— | C$_2$H$_5$ | H | H | CH$_3$ | |
| 14 | A1c | —NH— | Br | F | H | F | |
| 15 | A2b | —NH— | Cl | Cl | H | Cl | mp 295–296° C. |
| 16 | A1c | —S— | Cl | H | H | Cl | |
| 17 | A1c | —NH— | CH$_3$ | H | Cl | CH$_3$ | mp 142–143° C. |
| 18 | A1b | —O— | Cl | Cl | H | Cl | mp 238–239° C. |
| 19 | A2b | —NH— | Cl | CF$_3$ | H | Cl | mp 247–248° C. |
| 20 | A2b | —NH— | CF$_3$ | Cl | H | Cl | mp 275–276° C. |
| 21 | A1c | —NH—NH— | CH$_3$ | CH$_3$ | H | CH$_3$ | mp 178–179° C. |
| 22 | A2b | —NH— | Br | CH$_3$ | H | Br | mp 283–284° C. |
| 23 | A2b | —NH— | Br | isopropyl | H | Br | mp 263–264° C. |
| 24 | A1c | —NH—NH— | Cl | Cl | H | Cl | mp 252–253° C. | phases were combined. The insoluble material was filtered off and washed with diethylether, which dissolved most of the material into the filtrate. The filtrate was combined with the organic phases and this solution was dried, filtered and the solvent evaporated. The residue was purified over silica gel flash chromatography, eluting with 4:1 $CH_2Cl_2$:diethylether to 100% diethylether. The resulting material was recrystallized in tetrahydrofuran/ $CH_3CN$, filtered off and dried, yielding 0.36 g (67%) of 4-[[4-amino-6-[(2,4,6-trimethylphenyl)azo]-1,3,5-triazin-2-yl]aamino]benzonitrile (compound 69).

EXAMPLE B.2

O-(Trimethylsilyl)-hydroxylamine (0.0282 mol) was added to intermediate (5) (0.00282 mol) in 1,4-dioxane (10 ml). The reaction mixture was stirred at room temperature for 2 days. The solvent was evaporated. The residue was dissolved in ethyl acetate, washed with 1 N HCl, washed with a saturated aqueous $NaHCO_3$ solution and with brine, dried, filtered and the solvent was evaporated. The residue was purified by column chromatography over silica gel ((I) eluent gradient: $CH_2Cl_2/CH_3OH$ 98/2 to 96/4 and (II) eluent: $CH_2Cl_2/CH_3OH$ 100/0, 99/1 and 98/2). The desired fractions were collected and the solvent was evaporated. The residue was recrystallized from acetonitrile. The precipitate was filtered off and dried, yielding 0.32 g (29.2%) of 4-[[[6-(2,6-dichlorophenylamino)-4-(hydroxylamino)]-1,3, 5-triazin-2-yl]amino]-benzonitrile (compound 4).

EXAMPLE B.3

Tetrahydrofuran (10 ml) and 2,5-dimethyl-phenol (0.00818 mol) were added to NaH (0.00859 mol). The mixture was stirred for 30 minutes at room temperature. Then, a solution of intermediate (1) (0.00818 mol) in tetrahydrofuran (100 ml) was added. The reaction mixture was stirred for 16 hours. Then, the solvent was evaporated and $NH_3$ in 1,4-dioxane (50 ml) was added. The resulting reaction mixture was stirred for 16 hours. The solvent was evaporated; and, the resulting residue was treated with $H_2O/CH_2Cl_2$, stirred, and filtered. A precipitate formed in the filtrate and was filtered off, yielding 0.42 g of fraction 1. The resulting filtrate was dried over $K_2CO_3$ and concentrated. The residue was purified by flash column chromatography (eluent: $CH_3OH/CH_2Cl_2$ 2.5/97.5). The desired fractions were collected and the solvent was evaporated, yielding 2.89 g of fraction 2. Fractions 1 and 2 were combined and recrystallized from $CH_3CN$. The precipitate was filtered off and dried, yielding 1.16 g (42.7%) of 4-[[4-amino-6-(2,5-dimethylphenoxy)-1,3,5-triazin-2-yl] amino]benzonitrile (compound 2).

EXAMPLE B.4

To a reaction vessel under Ar were added the resin bound intermediate (1) as prepared in example A3 (0.00015 mol), a solution of silver triflate (0.075 g) in dimethylsulfoxide (1 ml), 4-bromo-2-chloro-6-methyl-phenol (0.0027 mol), dimethylsulfoxide (3 ml), 1.0 M sodium bis(trimethylsilyl) amide and disilazane (1,1,1-trimethyl-N-(trimethylsilyl)-silanamine, sodium salt) (3 ml). The reaction mixture was heated at 95° C. for 12 hours. The sample was filtered, and the resin was washed with N,N-dimethylformamide (3×), $CH_2Cl_2$, N,N-dimethylformamide, $CH_3OH$, and $CH_2Cl_2$ (3×). The sample was cleaved twice with 10% trifluoroacetic acid in $CH_2Cl_2$ (5 ml, then 3 ml). The solvent was evaporated under $N_2$. Purification by reverse phase HPLC yielded 0.0055 g of 4-[[4-amino-6-(4-bromo-2-chloro-6-methylphenoxy)-1,3,5-triazin-2-yl]amino]benzonitrile (compound 33).

EXAMPLE B.5

To a flask under Ar were added the resin bound intermediate (1) as prepared in example A3 (0.00015 mol), $CsCO_3$ (0.975 g), 4-chloro-2,6-dimethyl-phenol (0.0038 mol), dimethylsulfoxide (2 ml) and 1 ml of a solution of silver triflate (0.075 g) in dimethyl-sulfoxide (1 ml). Ar was bubbled through the reaction mixture for 1 minute. The flask was heated at 95° C. for 20 hours. The sample was then filtered, and washed with N,N-dimethylformamide (2×), water (3×), NN-dimethylformamide (2×), $CH_3OH$ (1 x), and $CH_2Cl_2$ (3×). The sample was then cleaved with 10% trifluoroacetic acid in $CH_2Cl_2$ (3 ml), yielding 0.0043 g of 4-[[4-amino-6-(4-chloro-2,6-dimethylphenoxy)-1,3,5-triazin-2-yl]amino] benzonitrile (compound 36).

EXAMPLE B.6

To a flask under Ar were added intermediate (1) (0.00752 mol), N,2,4,6-trimethyl-benzenamine (0.00752 mol) in 1,4-dioxane (20 ml) and N,N-diisopropylethylamine (0.00752 mol). The reaction mixture was stirred and refluxed for 20 hours and the solvent was evaporated. The residue was transferred into a pressure vessel with 0.5 M $NH_3$ in 1,4-dioxane (0.005 mol) and 2.0 M $NH_3$ in 2-propanol (0.040 mol) and this mixture was heated at 115° C. for 24 hours. The solvent was evaporated, the residue dissolved in $CH_2Cl_2$, washed with 1 N NaOH and water, dried with potassium carbonate, filtered, and the solvent evaporated. The residue was recrystallized two times with acetonitrile, filtered off and dried, yielding 1.0 g (37%) of 4-[[4-amino-6-[methyl(2,4,6-trimethylphenyl)amino]-1,3,5-triazin-2-yl] amino]benzonitrile (compound 73).

EXAMPLE B.7

4,6-dichloro-N-(2,6-dibromo-4-methylphenyl)-1,3,5-triazin-2-amine (0.00651 mol) was dissolved in 1,4-dioxane (30 ml). Sequentially, 4-amino-benzonitrile (0.0066 mol) and N,N-diisopropylethylamine (0.0066 mol) were added, and the clear solution was heated to reflux for 4 days. The reaction was allowed to cool to room temperature overnight. The mixture was diluted with ethylacetate and treated with cold 1 M NaOH. The layers were separated, and the organic phase was re-extracted with fresh 1 M NaOH. The combined aqueous phases were treated with solid NaOH to maintain pH>10 and backwashed with ethylacetate (2×). The combined organic phases were dried, filtered and concentrated. The residue was separated and purified by flash column chromatography over silica gel (eluent: $CH_2Cl_2$). The desired fractions were combined, treated with $CH_3CN$, triturated with $CH_3CN$, filtered off and dried, yielding 0.30 g (8.0%) of N,-[6-[(2,6-dibromo-4-methylphenyl)amino]-1, 3,5-triazine-2,4-diyl]bis[4-amino-benzonitrile] (compound 74).

EXAMPLE B.8

Intermediate (1), 1-(2,3-dihydro-4-hydroxy-7-methyl-1H-inden-5-yl)-ethanone, $Cs_2CO_3$, and 1,4-dioxane were added to a reaction vessel under Ar and heated at 100° C. for 48 hours while the sample was slightly vortexed. The sample was cooled, and $NH_3$ in isopropanol was added. The reaction was heated at 100IC in a sealed tube for 48 hours. The reaction was cooled, and water (3 ml) was added to dissolve $Cs_2CO_3$, and the sample was filtered and purified by HPLC, yielding 4-[[4-[(5-acetyl-2,3-dihydro-7-methyl-1H-inden-4-yl)oxy]-6-amino-1,3,5-triazin-2-yl]amino]benzonitrile (compound 84).

Tables 2 and 3 list the compounds of formula (I) which were prepared according to one of the above examples.

TABLE 2

| Comp No. | Ex. No. | X | R¹ | Rᵃ | Rᵇ | Rᶜ | Rᵈ | Rᵉ | melting point; salt form |
|---|---|---|---|---|---|---|---|---|---|
| 1 | B1a | —O— | H | Cl | H | H | H | Cl | 278–279° C. |
| 2 | B3 | —O— | H | CH₃ | H | H | CH₃ | H | 193–194° C. |
| 3 | B3 | —O— | H | CH₃ | H | H | H | CH₃ | 235–236° C. |
| 4 | B2 | —NH— | OH | Cl | H | H | H | Cl | 235–236° C. |
| 5 | B2 | —NH— | OH | CH₃ | H | H | H | CH₃ | 207–210° C. HCl (1:1) |
| 6 | B1a | —NH— | H | CH₃ | H | H | H | CH₃ | 242–244° C. HCl (1:1) |
| 7 | B1a | —NH— | H | Cl | H | H | H | CH₃ | 130–131° C. |
| 8 | B1a | —NH— | H | CH(CH₃)₂ | H | H | H | CH₃ | 253–254° C. |
| 9 | B1a or B1b | —NH— | H | CH₃ | H | CH₃ | H | CH₃ | 151–152° C. |
| 10 | B1c | —NH— | H | Cl | H | H | H | Cl | 144–145° C. |
| 11 | B2 | —NH— | OH | CH₃ | H | CH₃ | H | CH₃ | 247–248° C. |
| 12 | B1c | —NH— | H | C₂H₅ | H | H | H | C₂H₅ | 273–274° C. |
| 13 | B1c | —NH— | H | C(=O)CH₃ | H | H | CH₃ | H | 255–256° C. |
| 14 | B1b | —NH— | H | CH₃ | H | Br | H | CH₃ | 221–222° C. |
| 15 | B1b | —NH— | H | CH₃ | H | CH₃ | Br | CH₃ | 158–159° C. |
| 16 | B1b | —NH— | H | C₂H₅ | H | H | H | CH₃ | 222–223° C. |
| 17 | B1b | —NH— | H | Br | H | F | H | F | 233–234° C. |
| 18 | B1b | —NH— | H | Cl | H | Cl | H | Cl | 224–225° C. |
| 19 | B1b | —S— | H | Cl | H | H | H | Cl | 293–294° C. |
| 20 | B2 | —S— | OH | Cl | H | H | H | Cl | 145–147° C. |
| 21 | B1a | —NH—NH— | H | Cl | H | Cl | H | Cl | 258–259° C. |
| 22 | B1a | —NH—NH— | H | Cl | H | H | H | Cl | 246–247° C. |
| 23 | B2 | —NH— | OH | Cl | H | Cl | H | Cl | 262–263° C. |
| 24 | B1b | —O— | H | CH₃ | H | CH₃ | H | CH₃ | 236–237° C. |
| 25 | B2 | —O— | OH | CH₃ | H | CH₃ | H | CH₃ | 221–222° C. |
| 26 | B2 | —NH—NH— | OH | Cl | H | Cl | H | Cl | 175–176° C. |
| 27 | B1b | —NH— | H | Cl | H | CH₃ | H | Cl | 224–226° C. |
| 28 | B1b | —NH— | H | CH₃ | H | H | Cl | CH₃ | 230–231° C. |
| 29 | B2 | —NH— | OH | Cl | H | Cl | H | CH₃ | 268–269° C. |
| 30 | B1a | —O— | H | Cl | H | Cl | H | Cl | 260–261° C. |
| 31 | B2 | —NH— | OH | CH₃ | H | H | Cl | CH₃ | 174–175° C. |
| 32 | B2 | —O— | OH | Cl | H | Cl | H | Cl | 153–154° C. |
| 33 | B4 | —O— | H | Cl | H | Br | H | CH₃ | |
| 34 | B4 | —O— | H | Cl | H | Cl | H | CH₃ | |
| 35 | B4 | —O— | H | CH₃ | H | C(=O)CH₃ | H | CH₃ | |
| 36 | B5 | —O— | H | CH₃ | H | Cl | H | CH₃ | |
| 37 | B5 | —O— | H | CH₃ | H | Br | H | CH₃ | |
| 38 | B5 | —O— | H | Cl | H | Cl | H | H | |
| 39 | B5 | —O— | H | C(=O)CH₃ | H | Cl | H | Cl | |
| 40 | B5 | —O— | H | Br | H | Br | H | Br | |
| 41 | B5 | —O— | H | CH₃ | H | NO₂ | H | CH₃ | |
| 42 | B5 | —O— | H | Cl | Cl | Cl | Cl | Cl | |
| 43 | B5 | —O— | H | Cl | Cl | H | H | Cl | |
| 44 | B5 | —O— | H | F | H | F | H | F | |
| 45 | B5 | —O— | H | Cl | H | F | H | Cl | |
| 46 | B5 | —O— | H | OCH₃ | H | H | H | OCH₃ | |
| 47 | B5 | —O— | H | OCH₃ | H | CN | H | H | |
| 48 | B5 | —O— | H | Br | CH₃ | Cl | CH₃ | Br | |
| 49 | B5 | —O— | H | C(=O)CH₃ | H | F | H | F | |
| 50 | B5 | —O— | H | Br | CH₃ | Br | CH₃ | Br | |
| 51 | B5 | —O— | H | Br | H | CH₃ | H | Br | |
| 52 | B5 | —O— | H | CH₃ | CH₃ | Cl | H | CH₃ | |
| 53 | B5 | —O— | H | Cl | CH₃ | Cl | CH₃ | CH₃ | |
| 54 | B5 | —S— | H | Cl | H | Cl | H | H | |
| 55 | B5 | —S— | H | Cl | H | F | H | H | |
| 56 | B5 | —S— | H | Cl | H | Cl | Cl | H | |
| 57 | B5 | —S— | H | F | H | F | H | H | |
| 58 | B5 | —S— | H | CH₃ | H | CH₃ | H | CH₃ | |
| 59 | B5 | —S— | H | CH₃ | H | CH₃ | H | H | |
| 60 | B5 | —O— | H | CH₃ | H | I | H | CH₃ | |

TABLE 2-continued

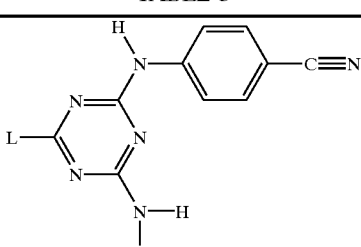

| Comp No. | Ex. No. | X | R¹ | Rᵃ | Rᵇ | Rᶜ | Rᵈ | Rᵉ | melting point; salt form |
|---|---|---|---|---|---|---|---|---|---|
| 61 | B5 | —NH— | H | $CH_3$ | H | $CH_3$ | $NH_2$ | $CH_3$ | |
| 62 | B8 | —O— | H | $CH_3$ | H | $CH_3$ | H | H | |
| 63 | B8 | —NH— | H | Cl | H | Br | H | $CH_3$ | |
| 64 | B8 | —NH— | H | $C_2H_5$ | H | Br | H | $C_2H_5$ | |
| 65 | B8 | —NH— | H | Cl | H | $CH_3$ | H | $CH_3$ | |
| 66 | B8 | —NH— | H | Cl | H | F | $CH_3$ | H | |
| 67 | B8 | —NH— | H | F | F | F | F | F | |
| 68 | B8 | —NH— | H | $OCH_3$ | H | $OCH_3$ | H | $OCH_3$ | |
| 69 | B1c | —N=N— | H | $CH_3$ | H | $CH_3$ | H | $CH_3$ | 315° C. |
| 70 | B1b | —NH— | H | Cl | H | $CF_3$ | H | Cl | 152–154° C. |
| 71 | B1b | —NH— | H | $CF_3$ | H | Cl | H | Cl | 158–160° C. |
| 72 | B1b | —NH— | H | Br | H | Br | H | Br | 167–169° C. |
| 73 | | —N($CH_3$)— | H | $CH_3$ | H | $CH_3$ | H | $CH_3$ | 251–252° C. |
| 74 | B7 | —NH— | p-cyano phenyl | Br | H | $CH_3$ | H | Br | 332–333° C. |
| 75 | B7 | —NH— | p-cyano phenyl | Br | H | isopropyl | H | Br | 315–316° C. |
| 76 | B1b | —NH— | H | Br | H | $CH_3$ | H | Br | 238–239° C. |
| 77 | B1b | —NH— | H | Br | H | isopropyl | H | Br | 158–160° C. |
| 78 | B5 | —O— | H | $CH_3$ | H | $NH_2$ | H | $CH_3$ | |
| 79 | B5 | —O— | H | $CH_3$ | H | C(=O)H | H | $CH_3$ | |
| 80 | B8 | —O— | H | F | F | OH | F | F | |
| 81 | B8 | —O— | H | $NH_2$ | H | Cl | $CH_3$ | Cl | |
| 82 | B8 | —NH— | H | C(=O)$OCH_3$ | H | $OCH_3$ | $OCH_3$ | $OCH_3$ | |

TABLE 3

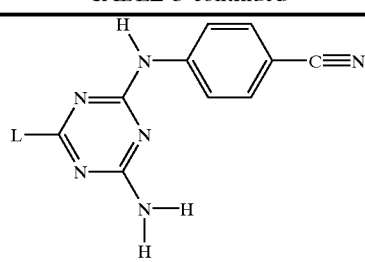

| Comp No. | Ex. No. | L |
|---|---|---|
| 83 | B8 | 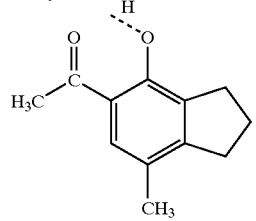 |
| 84 | B8 | 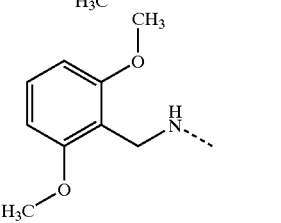 |
| 85 | B5 | |
| 86 | B5 | |

TABLE 3-continued

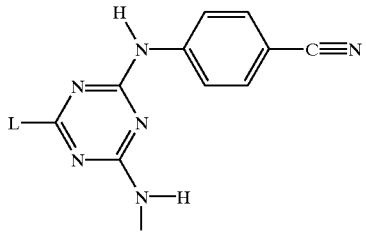

| Comp No. | Ex. No. | L |
|---|---|---|
| 87 | B5 | 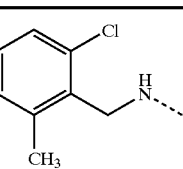 |

C. Pharmacological Example

EXAMPLE C.1

A rapid, sensitive and automated assay procedure was used for the in vitro evaluation of anti-HIV agents. An HIV-1 (wildtype IIIB) transformed T4-cell line, MT-4, which was previously shown (Koyanagi et al., *Int. J Cancer*, 36, 445–451, 1985) to be highly susceptible to and permissive for HIV infection, served as the target cell line. Inhibition of the HIV-induced cytopathic effect was used as the end point. The viability of both HIV- and mock-infected cells was assessed spectrophotometrically via the in situ reduction of 3-(4,5-dimethylthiazol-2-yl)-2,5-diphenyltetrazolium bromide (MTT). The 50% cytotoxic concentration ($CC_{50}$ in $\mu M$) was defined as the concentration of compound that reduced the absorbance of the mock-infected control sample by 50%. The percent protection achieved by the compound in HIV-infected cells was calculated by the following formula:

$$\frac{(OD_T)_{HIV} - (OD_C)_{HIV}}{(OD_C)_{MOCK} - (OD_C)_{HIV}} \text{ expressed in } \%,$$

whereby $(OD_T)_{HIV}$ is the optical density measured with a given concentration of the test compound in HIV-infected cells; $(OD_C)_{HIV}$ is the optical density measured for the control untreated HIV-infected cells; $(OD_C)_{MOCK}$ is the optical density measured for the control untreated mock-infected cells; all optical density values were determined at 540 nm. The dose achieving 50% protection according to the above formula was defined as the 50% inhibitory concentration ($IC_{50}$ in $\mu M$). The ratio of $CC_{50}$ to $IC_{50}$ was defined as the selectivity index (SI). The compounds of formula (1) were shown to inhibit HIV-1 effectively. Particular $IC_{50}$, $CC_{50}$ and SI values are listed in Table 4 hereinbelow.

TABLE 4

| Co. No. | $IC_{50}$ ($\mu M$) | $CC_{50}$ ($\mu M$) | SI |
|---|---|---|---|
| 1 | 0.003 | >20 | >6451 |
| 2 | 0.003 | 34.9 | 10750 |
| 3 | 0.003 | 33.8 | 10899 |
| 4 | 0.002 | 8.0 | 4187 |
| 5 | 0.002 | 7.8 | 3458 |
| 6 | 0.004 | 40.3 | 11518 |
| 7 | 0.005 | 49.9 | 10187 |
| 8 | 0.165 | 9.3 | 56 |
| 9 | 0.001 | 44.0 | 33826 |
| 10 | 0.003 | 6.1 | 2022 |
| 11 | 0.001 | 6.3 | 4480 |
| 12 | 0.021 | 30.0 | 1449 |
| 13 | 0.259 | >100 | >386 |
| 14 | 0.003 | 37.3 | 11844 |
| 15 | 0.003 | 1.7 | 498 |
| 16 | 0.006 | 8.1 | 1372 |
| 17 | 0.003 | 53.8 | 16311 |
| 18 | 0.008 | 45.6 | 6033 |
| 19 | 0.004 | 40.6 | 11285 |
| 20 | 0.003 | 11.7 | 3726 |
| 21 | 0.001 | 27.8 | 27789 |
| 22 | 0.003 | >100 | >33333 |
| 23 | 0.001 | 7.6 | 7614 |
| 28 | 0.005 | 42.8 | 9106 |
| 30 | 0.002 | 63.5 | 26488 |
| 31 | 0.005 | 9.9 | 1980 |
| 33 | 0.002 | >10.0 | >4761 |
| 34 | 0.001 | 4.8 | 3658 |
| 35 | 0.001 | 32.1 | 24712 |
| 36 | 0.003 | 7.6 | 2179 |
| 37 | 0.001 | 7.6 | 5035 |
| 38 | 0.007 | >100.0 | >14084 |
| 39 | >10 | <10 | 1 |
| 40 | 0.005 | >10.0 | >1851 |
| 41 | 0.002 | 12.2 | 6102 |
| 42 | 0.033 | >10.0 | >303 |
| 43 | 0.009 | 43.9 | 4668 |
| 44 | 0.005 | >100.1 | >19607 |
| 45 | 0.007 | 52.9 | 7258 |
| 46 | 0.031 | >100.0 | >3205 |
| 47 | 0.075 | >100.0 | >1340 |
| 48 | 0.019 | 8.7 | 456 |
| 49 | 0.076 | >99.9 | >1308 |
| 50 | 0.059 | 8.1 | 139 |
| 51 | 0.002 | 1.7 | 859 |
| 52 | 0.003 | 1.9 | 639 |
| 53 | 0.017 | 2.5 | 142 |
| 54 | 0.004 | 57.3 | 13349 |
| 55 | 0.004 | >99.9 | >27777 |
| 56 | 0.005 | 62.6 | 13059 |
| 57 | 0.015 | >100.0 | >6711 |
| 58 | 0.003 | 47.1 | 16244 |
| 59 | 0.002 | 48.5 | 26975 |
| 60 | 0.003 | 45.5 | 15172 |
| 61 | 0.005 | 94.6 | 20549 |
| 62 | 0.003 | 51.6 | 19110 |
| 63 | 0.003 | 48.0 | 16561 |
| 64 | 0.014 | 46.5 | 3393 |
| 65 | 0.001 | 48.5 | 80824 |
| 66 | 0.096 | >99.9 | >1037 |
| 67 | 0.111 | 45.6 | 412 |
| 68 | 0.015 | 63.9 | 4173 |
| 69 | 0.065 | >99.9 | >1547 |
| 70 | 0.003 | 15.6 | 4471 |
| 71 | 0.010 | 8.2 | 860 |
| 72 | 0.002 | 6.5 | 3259 |
| 73 | 0.003 | 51.7 | 16164 |
| 74 | 0.190 | 7.0 | 37 |
| 75 | 0.378 | 37.8 | 100 |
| 76 | 0.001 | 5.9 | 11848 |
| 77 | 0.003 | 47.0 | 17431 |
| 78 | 7.83 | 47.0 | 6 |
| 79 | 0.007 | 30.0 | 4534 |
| 80 | 85.5 | >85.5 | >1 |
| 81 | 2.68 | >99.1 | >37 |
| 82 | 1.49 | 99.6 | 67 |
| 83 | 0.473 | 59.6 | 126 |
| 84 | 0.001 | 54.1 | 45129 |
| 85 | 0.413 | 53.7 | 130 |

D. Composition Examples

The following formulations exemplify typical pharmaceutical compositions suitable for systemic administration to animal and human subjects in accordance with the present invention.

"Active ingredient" (A.I.) as used throughout these examples relates to a compound of formula (I) or a pharmaceutically acceptable addition salt thereof.

EXAMPLE D.1

Film-Coated Tablets

Preparation of Tablet Core

A mixture of 100 g of the A.I., 570 g lactose and 200 g starch was mixed well and thereafter humidified with a solution of 5 g sodium dodecyl sulfate and 10 g polyvinylpyrrolidone in about 200 ml of water. The wet powder mixture was sieved, dried and sieved again. Then there was added 100 g microcrystalline cellulose and 15 g hydrogenated vegetable oil. The whole was mixed well and compressed into tablets, giving 10.000 tablets, each comprising 10 mg of the active ingredient.

Coating

To a solution of 10 g methyl cellulose in 75 ml of denaturated ethanol there was added a solution of 5 g of ethyl cellulose in 150 ml of dichloromethane. Then there were added 75 ml of dichloromethane and 2.5 ml 1,2,3-propanetriol. 10 g of polyethylene glycol was molten and dissolved in 75 ml of dichloromethane. The latter solution was added to the former and then there were added 2.5 g of magnesium octadecanoate, 5 g of polyvinylpyrrolidone and 30 ml of concentrated color suspension and the whole was homogenated. The tablet cores were coated with the thus obtained mixture in a coating apparatus.

What is claimed is:

1. A compound of formula (II)

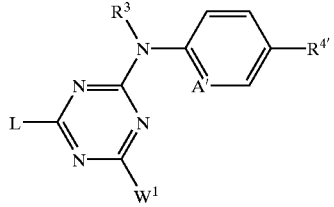

(II)

wherein $R^{4'}$ is cyano;

$R^3$ is hydrogen, A' is CH, $W^1$ is a halogen, and L is —X—$R^5$ or —X—Alk—$R^6$; wherein $R^5$ and $R^6$ each independently are indanyl, indolyl or phenyl; each of said indanyl, indolyl or phenyl may be substituted with one, two, three, four or five substituents each independently selected from halo, $C_{1-6}$alkyl, $C_{1-6}$alkyloxy, hydroxy, $C_{1-6}$alkylcarbonyl, $C_{1-6}$alkyloxycarbonyl, formyl, cyano, nitro, amino and trifluoromethyl;

Alk is $C_{1-4}$ alkanediyl; and

X is —$NR^3$—, —NH—NH—, —N=N—, —O—, —S—, —S(=O)— or —S(=O)$_2$—; provided that $R^5$ is other than p-cyano-phenyl, p-nitro-phenyl, p-methoxy-phenyl and p-aminocarbonyl-phenyl, and —X—Alk—$R^6$ is other that 2-(4-hydroxyphenyl) ethylamino.

* * * * *